(12) United States Patent
Kang

(10) Patent No.: US 12,708,522 B2
(45) Date of Patent: Aug. 18, 2026

(54) HEIGHT-ADJUSTABLE SPINAL FUSION CAGE

(71) Applicant: L&K BIOMED CO., LTD., Yongin-si (KR)

(72) Inventor: Gook Jin Kang, Seoul (KR)

(73) Assignee: L&K BIOMED CO., LTD., Yongin-si (KR)

( * ) Notice: Subject to any disclaimer, the term of this patent is extended or adjusted under 35 U.S.C. 154(b) by 146 days.

(21) Appl. No.: 17/927,592

(22) PCT Filed: Apr. 21, 2021

(86) PCT No.: PCT/KR2021/004990
§ 371 (c)(1),
(2) Date: Nov. 23, 2022

(87) PCT Pub. No.: WO2021/241890
PCT Pub. Date: Dec. 2, 2021

(65) Prior Publication Data

US 2023/0201003 A1 Jun. 29, 2023

(30) Foreign Application Priority Data

May 25, 2020 (KR) ........................ 10-2020-0062513

(51) Int. Cl.
*A61F 2/44* (2006.01)
*A61F 2/30* (2006.01)

(52) U.S. Cl.
CPC .. *A61F 2/4465* (2013.01); *A61F 2002/30476* (2013.01); *A61F 2002/30553* (2013.01); *A61F 2002/30556* (2013.01)

(58) Field of Classification Search
CPC .............................. A61F 2/4455–2/447; A61F 2250/0004–2250/001; A61F 2250/0048
See application file for complete search history.

(56) References Cited

U.S. PATENT DOCUMENTS 9,585,762 B2 3/2017 Suddaby et al.
2003/0208275 A1* 11/2003 Michelson .............. A61F 2/446 623/17.15

(Continued)

FOREIGN PATENT DOCUMENTS

JP 2014-514019 A 6/2014
JP 2019-84362 A 6/2019

(Continued)

OTHER PUBLICATIONS

International Search Report for PCT/KR2021/004990 dated Jul. 27, 2021.

(Continued)

*Primary Examiner* — Julianna N Harvey
(74) *Attorney, Agent, or Firm* — Sughrue Mion, PLLC

(57) ABSTRACT

The present invention relates to a spinal fusion cage which is inserted between vertebral bodies at the lowest height and is height-adjustable in the inserted state, and has improved fixing strength by insertion of a bone screw through an end plate, wherein cages having heights within a predetermined range can be replaced by a single cage. Therefore, manufacturers can reduce the number of product groups that need to be produced, and can also reduce product stock. In addition, unlike the conventional cages having preset heights at regular intervals, the height can be linearly adjusted according to the distance between the vertebral bodies of a patient, and thus surgery can be performed using the cage adjusted to an optimum height according to the patient's condition.

25 Claims, 22 Drawing Sheets

(56) References Cited

U.S. PATENT DOCUMENTS

| | | | | |
|---|---|---|---|---|
| 2008/0140207 | A1 * | 6/2008 | Olmos | A61F 2/4455 623/17.11 |
| 2012/0059472 | A1 * | 3/2012 | Weiman | A61F 2/44 623/17.12 |
| 2012/0185049 | A1 * | 7/2012 | Varela | A61F 2/447 623/17.16 |
| 2012/0226357 | A1 * | 9/2012 | Varela | A61F 2/447 623/17.16 |
| 2012/0323328 | A1 * | 12/2012 | Weiman | A61F 2/447 623/17.16 |
| 2014/0039622 | A1 * | 2/2014 | Glerum | A61F 2/447 623/17.15 |
| 2014/0277487 | A1 | 9/2014 | Davenport | |
| 2017/0143507 | A1 * | 5/2017 | Flower | A61F 2/447 |
| 2017/0151065 | A1 | 6/2017 | Warren et al. | |
| 2017/0224504 | A1 * | 8/2017 | Butler | A61F 2/447 |
| 2017/0224505 | A1 * | 8/2017 | Butler | A61F 2/44 |
| 2017/0258605 | A1 | 9/2017 | Blain et al. | |
| 2018/0296361 | A1 * | 10/2018 | Butler | A61F 2/4455 |
| 2019/0038435 | A1 | 2/2019 | Daffinson et al. | |
| 2019/0133782 | A1 * | 5/2019 | McLaughlin | A61F 2/4425 |
| 2020/0129307 | A1 * | 4/2020 | Hunziker | A61F 2/447 |
| 2020/0383798 | A1 * | 12/2020 | Butler | A61F 2/446 |
| 2021/0315707 | A1 * | 10/2021 | Keller | A61F 2/4455 |
| 2022/0211514 | A1 * | 7/2022 | Spitler | A61F 2/4425 |
| 2023/0046487 | A1 * | 2/2023 | Kang | A61F 2/447 |

FOREIGN PATENT DOCUMENTS

| | | | |
|---|---|---|---|
| JP | 2019-88791 | A | 6/2019 |
| KR | 10-2008-0047276 | A | 5/2008 |
| KR | 10-2014-0009453 | A | 1/2014 |
| KR | 10-2020-0025453 | A | 3/2020 |
| KR | 10-2117224 | B1 | 5/2020 |
| KR | 10-2147077 | B1 | 8/2020 |
| WO | 2021/071150 | A1 | 4/2021 |

OTHER PUBLICATIONS

Extended European Search Report issued May 27, 2024 in European Application No. 21811832.1.

Office Action issued Feb. 9, 2024 in Australian Application No. 2021278632.

* cited by examiner 102
100
110
106
104

HEIGHT-ADJUSTABLE SPINAL FUSION CAGE

TECHNICAL FIELD

The present invention relates to a height-adjustable spinal fusion cage. More specifically, the present invention relates to a spinal fusion cage which is inserted between vertebral bodies at the lowest height and is height-adjustable in the inserted state, and in particular, has improved fixing strength by insertion of a bone screw through an end plate.

BACKGROUND ART

The vertebral body includes 32 to 35 vertebrae and intervertebral disks, which are simply called disks, between the vertebrae, and is the central part of the body that connects the skull at the top and the pelvis at the bottom.

The vertebra is composed of 7 cervical vertebrae, 12 thoracic vertebrae, 5 lumbar vertebrae, 5 sacral vertebrae (sacrum), and 3 to 5 coccygeal vertebrae (coccyx). In adults, the five sacral vertebrae fuse into one sacrum, and the three to five coccygeal vertebrae fuse into one coccyx.

Spinal fusion is a method of treating serious spinal diseases that last for a long time. In spinal fusion surgery, an intervertebral disk is removed, and a cage is inserted as a substitute between adjacent vertebral bodies to join the adjacent vertebral bodies together.

The spinal fusion methods for the lumbar spine may be classified, depending on the insertion direction of a cage, into posterior lumbar interbody fusion (PLIF), transforaminal lumbar interbody fusion (TLIF), lateral lumbar interbody fusion (LLIF), oblique lumbar interbody fusion (OLIF), anterior lumbar interbody fusion (ALIF), etc.

Posterior lumbar interbody fusion (PLIF) is a method of making an incision along the midline of the lumbar spine to entirely expose a vertebra, removing a posterior portion of the vertebra, removing a disk, and inserting PLIF cages.

Posterior lumbar interbody fusion (PLIF) is the oldest method among lumbar interbody fusion methods, and is necessary when fusing two or three vertebrae together. However, posterior lumbar interbody fusion (PLIF) has disadvantages such as a high possibility of adhesions at the nerves, ligaments, and muscles due to surgical procedures, a long recovery time due to a large incision area, and serious sequelae in some patients.

PLIF cages, a pair of small cages configured to be arranged at the left and right sides, are smallest among all the cages used for spinal fusion.

Transforaminal lumbar interbody fusion (TLIF) is a surgical method in which small incisions are made along both sides of a spine muscle to minimally expose the body of a vertebra, and then while removing a portion of the vertebra to expose a neural foramen, a TLIF cage is inserted instead of a disk. This surgical technique is advantageous in terms of less bleeding and a short operation time and is suitable for one joint, but PLIF is required when treating multiple sites. Most TLIF cages are arc shaped, and thus the convex portion of a TLIF cage is oriented toward the abdomen by inserting and rotating the TLIF cage between vertebral bodies. TLIF cages are larger than PLIF cages, but the supporting areas of TLIF cages are smaller than those of LLIF cages or ALIF cages, which will be mentioned later.

Anterior lumbar interbody fusion (ALIF) has several advantages, such as quick recovery from surgery and a low possibility of adhesions. However, ALIF requires a highly advanced skill in making an incision in the anterior (abdomen) and accessing the spine while dislodging the internal organs. ALIF cages have an advantage of having the largest support areas among all interbody fusion cages.

Among these ALIF cages, a stand-alone cage (integrated cage) having a hole through which a screw can be inserted and fixed into the vertebral body to prevent the cage from being separated after the procedure has been disclosed (US2014-0277487A).

In addition, U.S. Pat. No. 9,585,762 and US2019-0133782A disclose a stand-alone ALIF cage which is height-adjustable. However, U.S. Pat. No. 9,585,762 discloses that the height is adjusted by a vertical ratchet 302, so substantially it is characterized by adjusting the angle, not the height. US2019-0133782A discloses that the height is adjusted, but there is a problem that it is not easy to manufacture because the structure is too complicated.

PRIOR ART REFERENCE

Patent Document (Patent Document 1) U.S. Pat. No. 9,585,762
(Patent Document 2) US2019-0133782A
(Patent Document 3) US2014-0277487A

DETAILED DESCRIPTION OF INVENTION

Technical Task

An object of the present invention derived for solving the above-mentioned problems is to provide a spinal fusion cage which is inserted between vertebral bodies at the lowest height, is height-adjustable in the inserted state, and can stably support the movement of a pair of end plates.

Means for Solving Technical Task

In order to achieve the above object, the present invention provides: a spinal fusion cage, comprising: a first end plate and a second end plate which are in contact with adjacent vertebral bodies; a distal movable block connected to be movable relative to distal portions of the first end plate and the second end plate; a proximal movable block connected to be movable relative to proximal portions of the first end plate and the second end plate; an adjustment member capable of adjusting the distance between the distal movable block and the proximal movable block by adjusting the distance between the proximal movable block and the distal movable block by rotation; and a vertical guide portion disposed in the first end plate and the second end plate, to support a load in the longitudinal direction or width direction of the first end plate and the second end plate, wherein a block slider is formed on the distal movable block and the proximal movable block, and a plate slider slidable relative to the block slider is formed on the first and second end plates, and the distance of the block slider of the distal movable block from the axis of the adjustment member in the width direction is longer than the distance of the block slider of the distal movable block from the axis of the adjustment member in the width direction.

A block auxiliary slider is disposed around the distal movable block, and a plate auxiliary slider sliding on the auxiliary block slider is formed on the first and second end plates.

The block auxiliary slider is disposed at the end of the distal movable block in the width direction.

The block auxiliary slider is disposed in a direction opposite to the block slider.

The adjustment member has a threaded portion screw-coupled to the distal movable block on an end thereof, and a rotation support place fixed to be rotatable relative to the proximal movable block on the other end thereof, wherein a rotation support member is positioned in the rotation support place through the proximal movable block.

The vertical guide portion has a first vertical guide formed in a thickness direction of the first end plate or the second end plate, and a second vertical guide formed in the thickness direction of the first end plate or the second end plate to be slidable with the first vertical guide, wherein two pairs of the vertical guides are arranged, one pair of the vertical guides is arranged on one side of the first end plate and the second end plate in the width direction, and the other pair of the vertical guides is arranged on the other side of the first end plate and the second end plate in the width direction.

The first vertical guide is a pillar protruding from the first or second end plate in the thickness direction, and the second vertical guide has a channel surrounding part of the outer surface of the pillar.

The channel is formed by a first recessed portion arranged concavely in the first or second end plate in the width direction, and a second recessed portion formed by an extension portion protruding from the recessed portion in the thickness direction of the first or second end plate.

An accommodation portion accommodating the extension portion is formed around the pillar.

The first recessed portion is formed concavely by a first recessed wall disposed on the side of the proximal portion, a second recessed wall spaced apart from the first recessed wall and disposed on the side of the distal portion, and a third recessed wall connecting the first recessed wall and the second recessed wall.

The thickness of the pillar in the width direction is the same as the depth of the first recessed portion in the width direction, and the thickness of the pillar in the longitudinal direction is the same as the distance between the first recessed wall and the second recessed wall in the longitudinal direction.

The second recessed portion is formed by an extension portion including a first extension wall protruding from the first or second end plate in the thickness direction and disposed on the side of the proximal portion, a second extension wall protruding from the first or second end plate in the thickness direction and disposed on the side of the distal portion, and a third extension wall protruding from the first or second end plate in the thickness direction and connecting the first extension wall and the second extension wall, wherein the first extension wall and the first recessed wall form a plane, the second extension wall and the second recessed wall for a plane, and the third extension wall and the third recessed wall form a plane.

The depth of the second recessed portion in the width direction is smaller than the depth of the first recessed portion in the width direction.

A guide groove guiding the insertion of the pillar is formed around the first recessed portion.

The sum of the thickness of the first extension wall and the second extension wall in the longitudinal direction is greater than or equal to the thickness of the pillar in the longitudinal direction.

The thickness of the third extension wall in the width direction is the same as the thickness of the pillar in the width direction.

A through-hole is disposed on the side portion of the first and second end plates.

A center groove is disposed at an end of the proximal side of the first or second end plate.

A cover member is installed on the proximal movable block.

The cover member comprises a cover plate covering the center groove, and a cover bolt penetrating the cover plate to be fixed to the proximal movable block.

A holding groove for holding is formed on the cover plate.

The spinal fusion cage comprises: a bone screw inserted through a bone screw hole formed in the first end plate and the second end plate; and a locking member fastened to the proximal movable block to prevent the bone screw from being separated.

The locking member comprises a locking plate covering the bone screw, and a locking bolt penetrating the locking plate to be fixed to the proximal movable block, wherein a locking bolt fastening portion capable of coupling the locking bolt to a front end of the adjustment member is formed on the proximal movable block.

A locking projection protruding toward the bone screw is formed at a rear end of the locking plate.

The locking bolt adds pressure by contacting the adjustment member when coupled.

Effect of Invention

According to the present invention, cages having heights within a given range can be replaced with one cage. Therefore, manufacturers may reduce the number of product groups and the amount of inventory. Additionally, since the height of the cage is linearly adjustable according to the distance between the vertebral bodies of patients unlike conventional cages having heights preset at predetermined intervals, surgery may be performed at an optimal height according to the conditions of patients.

Also, since the cage is inserted at the lowest height, the burden of separately producing test inserts according to the existing proper intervertebral spacing may be reduced, and the effort of securing an insertion space while inserting a plurality of test inserts sequentially may be reduced from the doctor's point of view.

BRIEF DESCRIPTION OF DRAWINGS

Figure 42:
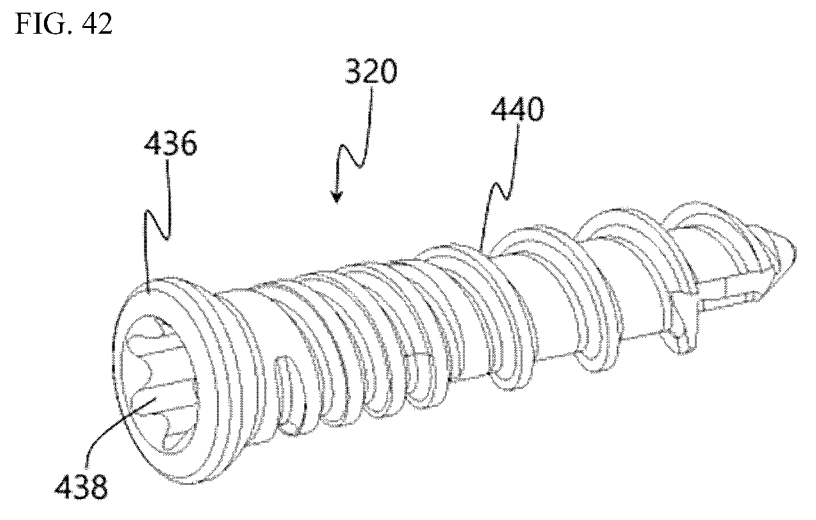

FIG. 42 is a perspective view of the bone screw of the second embodiment.

BEST MODE FOR CARRYING OUT THE INVENTION

Figures 1, 2:
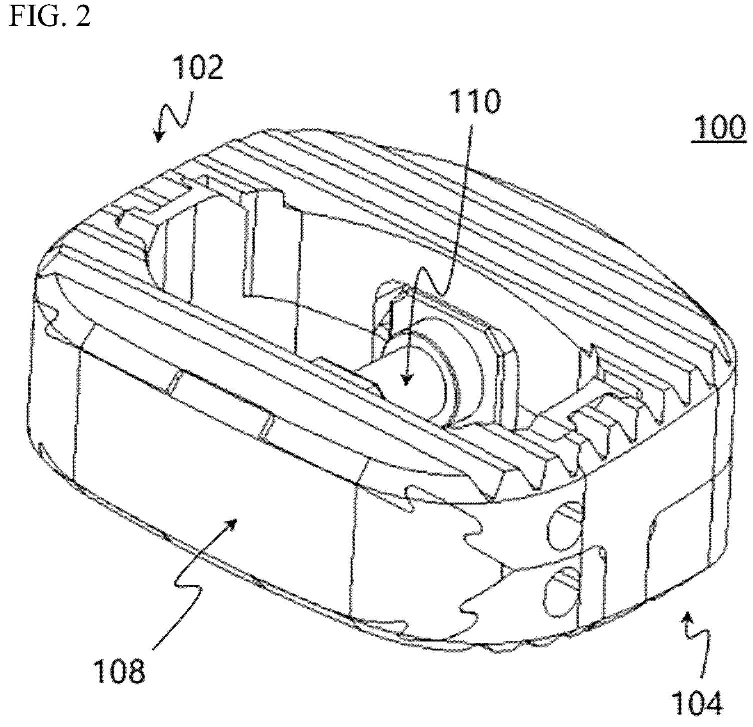
FIG. 1 is a top front perspective view of a spinal fusion cage according to a first embodiment of the present invention in the lowest state.
FIG. 2 is a top rear perspective view of the spinal fusion cage of FIG. 1.

Hereinafter, preferred embodiments of the present disclosure will be described with reference to the accompanying drawings. In the drawings, the same elements may be denoted with the same reference numerals even though the elements are shown in different drawings, and detailed descriptions related to well-known functions or configurations will be ruled out in order not to unnecessarily obscure subject matters of the present disclosure.

The directions as used herein will be defined. A distal direction means a direction into which the spinal fusion cage is inserted, and a proximal direction means a direction opposite to the distal direction. A longitudinal direction means a virtual linear direction connecting the distal direction and proximal direction. A thickness direction means a thickness direction of the end plate, i.e., a virtual linear direction toward the vertebrae above and below. A width direction, a direction perpendicular to both the longitudinal direction and thickness direction, means a horizontal direction of the end plate.

FIGS. 1 to 9 illustrate the entire spinal fusion cage 100 according to the first embodiment. FIGS. 8 to 21 illustrate each element of the spinal fusion cage 100. FIGS. 22 to 28 illustrate the entire spinal fusion cage 300 according to the second embodiment. FIGS. 29 to 42 illustrate each element of the spinal fusion cage 300.

The spinal fusion cage 100 of the first embodiment and the spinal fusion cage 300 of the second embodiment are different in parts related to the bone screw, and other parts are the same. Accordingly, the spinal fusion cage 100 of the first embodiment and the spinal fusion cage 300 of the second embodiment will be described together, and differences will be described later.

The spinal fusion cage 100, 300 includes a first end plate 102, 302 and a second end plate 104, 304 which face each other in a vertical direction, a distal movable block 108, 308 and a proximal movable block 106, 306 which are arranged between the first end plate 102, 302 and the second end plate 104, 304 to move along the distance between the first end plate 102, 302 and the second end plate 104, 304, and an adjustment member 110, 310 penetrating the proximal movable block 106, 306 to be connected to the distal movable block 108, 308.

Further, the spinal fusion cage includes a vertical guide portion which is disposed in the first end plate 102, 302 and the second end plate 104, 304 to support a load in the longitudinal direction or width direction of the first end plate 102, 302 and the second end plate 104, 304.

The first end plate 102, 302 and the second end plate 104, 304 have a first plate body 122, 322 and a second plate body 146, 346 which have tooth-shaped projections on the surface in contact with the vertebral bodies. The tooth-shaped projections are formed to prevent separation from the vertebral bodies, and various modifications may be made. Also, a first window 145, 345 and a second window 172, 372 for inserting a bone graft are respectively formed in a center portion of the first plate body 122, 322 and the second plate body 146, 346.

As illustrated in FIGS. 10 and 11 or 29 and 30, a proximal movable block place 130, 330 is formed on the first plate body 122, 322 in the proximal direction along the longitudinal direction, and a distal movable block place 138, 338 is formed in the distal direction. A plate slope portion 128, 328 is formed extending from the proximal movable block place 130, 330, and a pair of plate sliders 132, 332 facing each other are formed on both sides of the plate slope portion 128, 328.

Similarly, as illustrated in FIGS. 12 and 13 or 31 and 32, a proximal movable block place 156, 356 is formed on the second plate body 146, 346 in the proximal direction along the longitudinal direction, and a distal movable block place 164, 364 is formed in the distal direction. A plate slope portion 154, 354 is formed extending from the proximal movable block place 156, 356, and a pair of plate sliders 158, 358 facing each other are formed on both sides of the plate slope portion 154, 354.

Plate slope portions 139, 165, 339, 365 are formed around the distal movable block places 138, 156, 338, 356. The plate slope portions 139, 165, 339, 365 are formed on both ends of the distal movable block places 138, 164, 338, 364, and plate sliders 142, 168, 342, 368 are respectively formed to the outside of the plate slope portions 139, 165, 339, 365. Plate auxiliary sliders 144, 170, 344, 370 may be formed to face the plate sliders 142, 168, 342, 368 to the outside of the plate sliders 142, 168, 342, 368.

When the spinal fusion cage 100, 300 is used in ALIF, due to the structure of the spine, the proximal side is thicker than the distal side in the first end plate 102, 302 and the second end plate 104, 304. Therefore, when a load is applied in the thickness direction, width direction or longitudinal direction, the stress flow may be concentrated on the distal side which is relatively thinner. Accordingly, in order to make the stress distribution even, it is preferable to add the plate auxiliary sliders 144, 170, 344, 370.

The plate slider 132, 158, 332, 358 formed at the proximal portion and the plate slider 142, 168, 342, 368 formed at the distal portion are formed to be sloped in a manner approaching the center of the first plate body 122, 322 or the second plate body 146, 346 as they go away from the surface of the first plate body 122, 322 in the thickness direction.

Plate auxiliary support portions 133, 157, 333, 357 are formed around the outer side of the plate sliders 132, 158, 332, 358 formed in the proximal portion in the width direction. The plate auxiliary support portions 133, 157, 333, 357 extend the support area with the block auxiliary support portions 181, 381 of the proximal movable block 106 so that the load can be delivered more stably.

Reinforcing slope portion places 140, 166, 340, 366 are formed extending from the distal movable block places 138, 164, 338, 364. The reinforcing slope portion places 140, 166, 340, 366 may have the following reinforcing slope portions 200, 400 placed therein, and prevent the reinforcing slope portions 200, 300 from interfering with the first plate body 122, 322 or the second plate body 146, 346 when the distal movable blocks 108, 308 are moved.

A first side hole 123, 323 and a second side hole 153, 353 are respectively formed in the side portions of the first plate body 122, 322 and the second plate body 146, 346. The first side hole 123, 323 and the second side hole 153, 353 allow communication with the inner space and the surrounding of the spinal fusion cage 100, 300, so that the bone graft is discharged to the outside when a bone graft is introduced into the spinal fusion cage 100, 300 to connect the inside and outside of the spinal fusion cage 100, 300.

The plate sliders 132, 158, 332, 358 disposed in the proximal direction and the plate sliders 142, 168, 342, 368 disposed in the distal direction have different distance in the width direction with respect to the axis of the adjustment member 110, 310. In other words, the distance of the plate sliders 132, 158, 332, 358 disposed in the proximal direction from the axis of the adjustment member 110, 310 in the width direction is longer than the distance of the plate sliders 142, 168, 342, 368 disposed in the distal direction from the axis of the adjustment members 100, 300 in the width direction.

Figure 3:
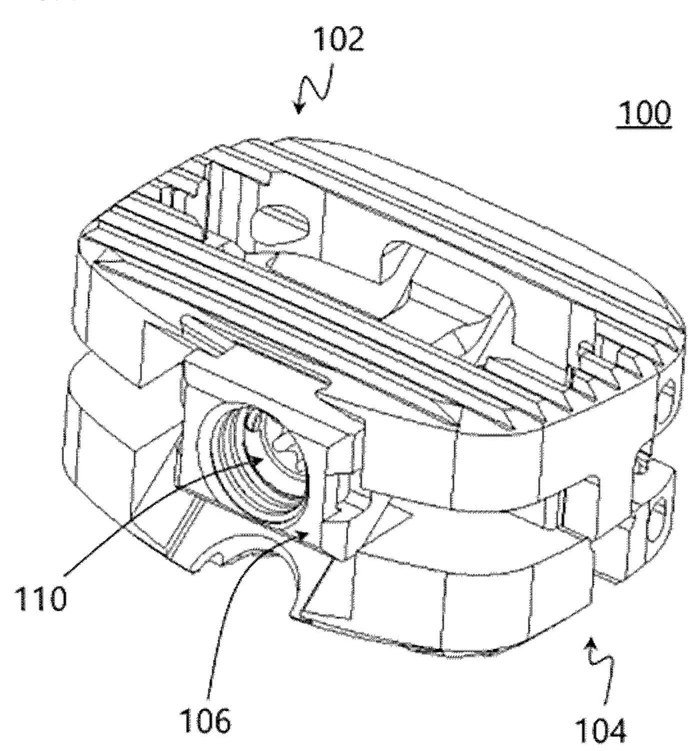
FIG. 3 is a top front perspective view in the highest state of the first embodiment.
Figure 4:
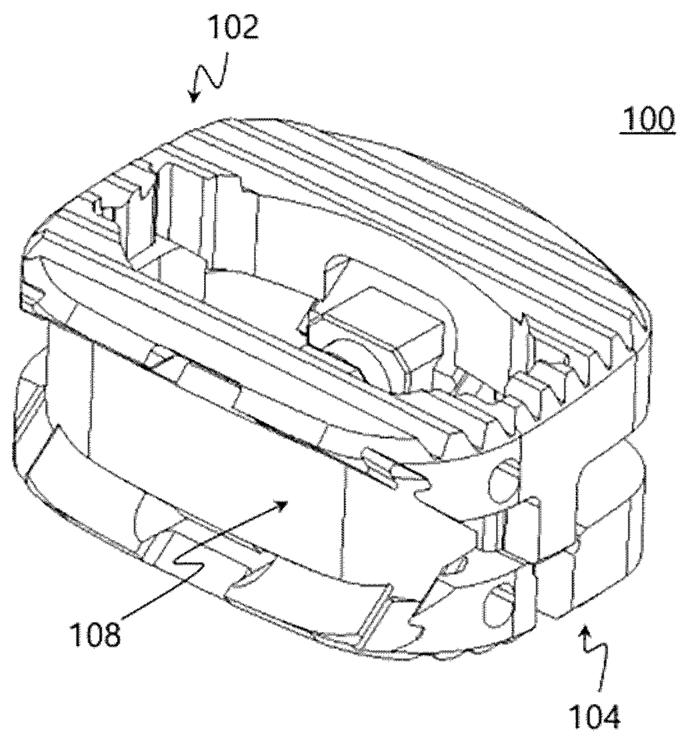
FIG. 4 is a top rear perspective view of the spinal fusion cage of FIG. 3.
Figure 24:
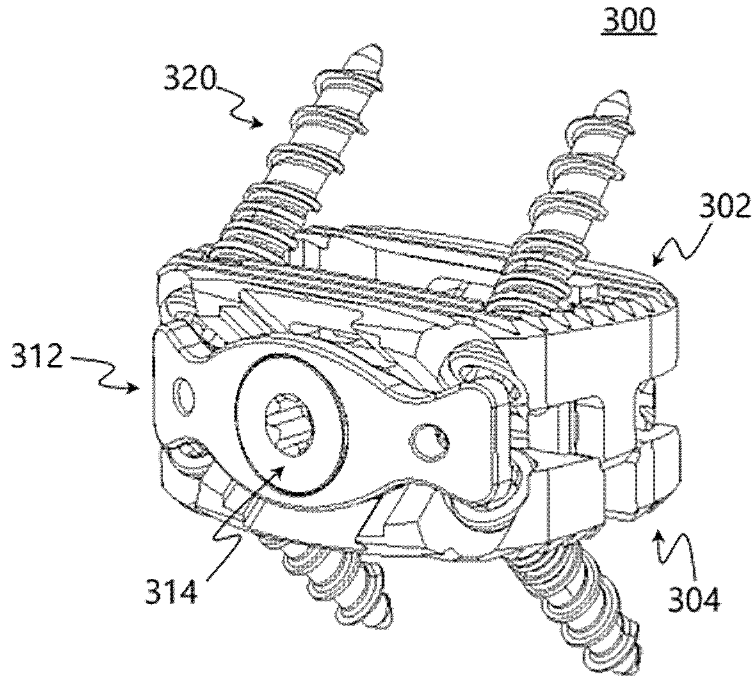
FIG. 24 is a top front perspective view in the highest state of the second embodiment.
Figures 25, 26:
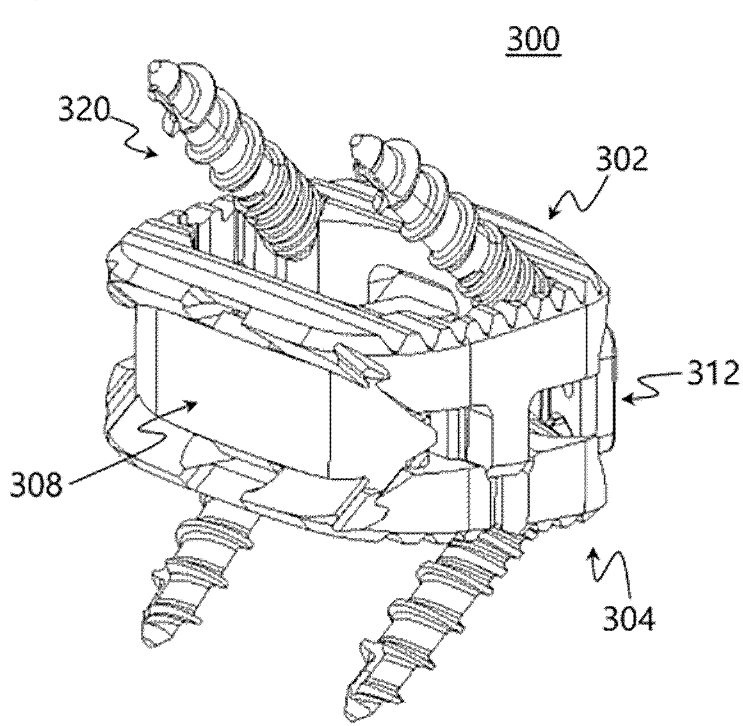
FIG. 25 is a top rear perspective view of the spinal fusion cage of FIG. 3.
FIG. 26 is an exploded top front perspective view of the spinal fusion cage of the second embodiment.

In particular, when the length in the width direction is long such as in ALIF, the proximal movable block 106, 306 supporting the adjustment member 110, 310 must have a smaller length in the width direction with respect to the axis of the adjustment member 110, 310, in order to secure a wider space around the proximal movable block 106, 306. Therefore, as illustrated in FIG. 3 or 24, it is more convenient to additionally insert a bone graft around the proximal movable block 106, 306 into the internal space of the spinal fusion cage 100, 300 and increase the amount of insertion in a state in which the height of the spinal fusion cage 100, 300 is high.

Figure 23:
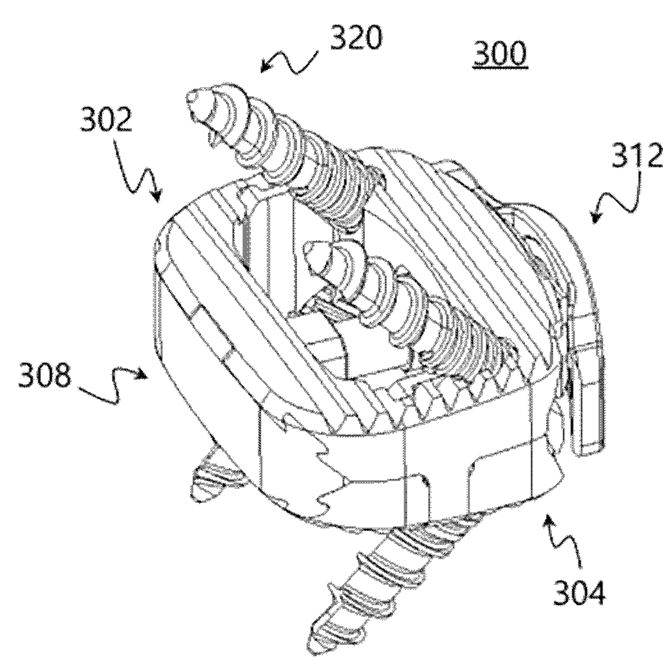
FIG. 23 is a top rear perspective view of the spinal fusion cage of FIG. 1.

On the contrary, as illustrated in FIG. 2 or 23, since it is inserted between the vertebral body in a state in which the height is minimum, the spinal fusion cage 100, 300 must be formed in a structure with no gaps in the distal direction. Accordingly, the length of the distal movable block 108, 308 in the width direction is formed to be approximately the same as the length between the side of the distal end of the first end plate 102, 302 and the side of the distal end of the second plate 104, 304 in the width direction.

At this time, in order for the proximal movable block 106, 306 to have a smaller length in the width direction with respect to the axis of the adjustment member 110, 310, the block slider 180, 380 has a length smaller in the width direction with respect to the axis of the adjustment member 110, 310. In order to supplement the stability of the structure, the block slider 204, 504 formed on the distal movable block 108, 308 is formed on both ends of the distal movable block 108, 308 so as to have a length larger in the width direction with respect to the axis of the adjustment member 110, 310. Therefore, the block slider 180, 380 at the side of the proximal end and the block slider 204, 404 at the side of the distal end may be formed in a trapezoidal shape in which the side of the proximal end is narrow and the side of the distal end is long.

As illustrated in FIGS. 15 and 16 or 34 and 35, the proximal movable block 106, 306 is formed with a block slope portion 174, 374 at the side of the proximal end with respect to a proximal connecting tube 190, 390 having an adjustment member hole 188, 388 into which the adjustment member 110, 310 is inserted and supported. A block slider 180, 380 slidably coupled to plate sliders 132, 158, 332, 358 formed on the first and second end plates 102, 104, 302, 304 are disposed on both sides of the block slope portion 174. The adjustment member hole 188, 388 has a support portion 184, 384 supporting in contact with the adjustment member 110, 310, and a support jaw 186, 386 formed at the side of the distal end of the support portion 184, 384 in order to prevent the separation of the adjustment member 110, 310.

A pinhole 178, 378 is formed on the side portion of the proximal movable block 106, 306 to prevent separation at the side of the proximal end of the adjustment member 110, 310 positioned on the support portion 184, 384. A tool place 176, 376 is formed on the side portion of the proximal movable block 106, 306 so that the tool can fix the spinal fusion cage 100, 300. A bolt fastening portion 182, 382 which may be connected to other implants such as tools or plates is formed on the proximal side of the region into which the adjustment member 110, 310 is inserted.

As illustrated in FIGS. 17 and 18 or 36 and 37, the distal movable block 108, 308 has a distal connecting tube 198, 398 having a movable block threaded portion 202, 402 screw-coupled to the adjustment member 110, 310 formed in the center portion, and has a wing portion 196, 396 on both sides of the distal connecting tube 198, 398. A block slope portion 194, 394 is formed on the wing portion 196, 396, and a block slider 204, 404 is disposed on both sides of the wing portion 196, 396. A block auxiliary slider 206, 406 is formed to the outside of the block slider 204, 404. The block slider 204, 404 and the block auxiliary slider 206, 406 are respectively slidably coupled to the plate slider 142, 168, 342, 368 and the plate auxiliary slider 144, 170, 344, 370 of the first and second end plates 102, 104, 302, 304.

The distal movable block 108, 308 has a distal wall 192, 392 for easy insertion between the vertebral bodies, and the distal wall 192, 392 is integrally formed with the block slope portion 194, 394. In a state in which the height is the lowest, the end wall 192, 392 comes into contact with the end of the first end plate 102, 302 and the end of the second end plate 104, 304 to constitute a single insertion portion as a whole. In particular, a distal curved surface 208, 408 is formed on both sides of the distal wall 192, 392 to make the insertion easier.

A reinforcing slope portion 200, 400 is formed in the center of the distal movable block 108, 308 to serve the role of reinforcing the load supported by the block slider 204, 404 and the block auxiliary slider 206, 406. As described above, the reinforcing slope portion 200, 400 is stably positioned while being inserted into the reinforcing slope portion place 140, 166, 340, 366 of the first end plate 102, 302 and the second end plate 104, 304.

The distal movable block 108, 308 and the proximal movable block 106, 306 have a substantially wedge-shaped structure, and are raised or lowered by adding pressure to the first end plate 102, 302 and the second end plate 104, 304.

Figure 19:
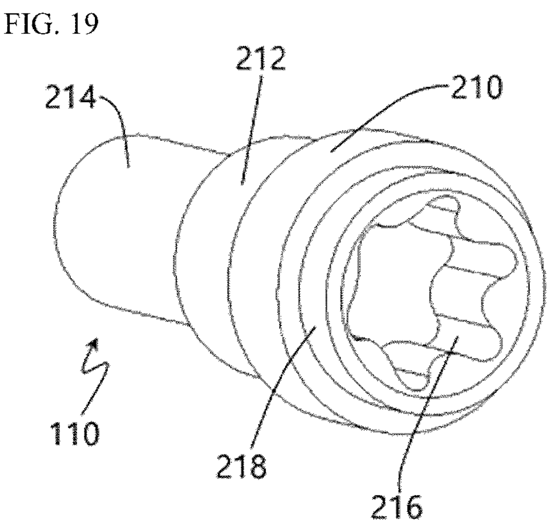
FIG. 19 is a perspective view of an adjustment member of the first embodiment.
Figure 38:
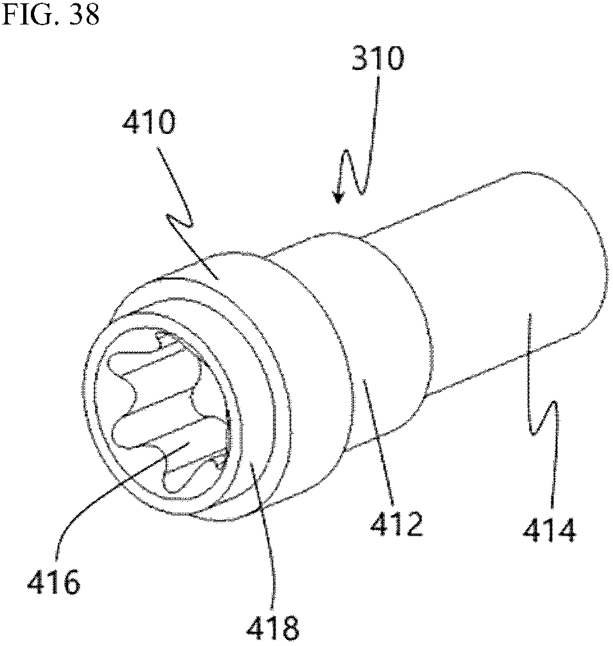
FIG. 38 is a perspective view of the adjustment member of the second embodiment.

As illustrated in FIG. 19 or 38, the adjustment member 110, 310 may have substantially a bolt shape. In other words, the adjustment member 110, 310 has an adjustment member support surface 210, 410 and an adjustment threaded portion 214, 314. A connection portion 212, 412 may be formed between the adjustment member support surface 210, 410 and the adjustment threaded portion 214, 414. A pin place 218, 418 is formed on the proximal side of the adjustment member support surface 210, 410, and a tool groove 216, 416 is formed in the center thereof to provide driving force to the adjustment member 110, 310. The adjustment threaded portion 214, 414 is a male screw, but detailed expressions are omitted in the drawings.

The adjustment member support surface 210, 410 is rotatably supported in contact with the support portion 184 of the distal movable block 108, 308. The adjustment threaded portion 214, 414 is screw-coupled to the movable block threaded portion 202, 402 of the adjustment member 110, 310. The movable block threaded portion 202, 402 is a female screw, but detailed expressions are omitted in the drawings. Since the spare surface at the side of the distal end of the adjustment member support surface 210, 410 contacts the support jaw 186, 386, the adjustment member 110, 310 is not separated from the distal movable block 108, 308 in the distal direction. Since a pin member 118, 318 is inserted into the pin place 218, 418 and positioned in the pin place 218, 418, the adjustment member 110, 310 is not separated in the proximal direction of the distal movable block 108, 308.

As a result, the adjustment member 120, 320 is rotatable in place inside the adjustment member 110, 310.

Figure 10:
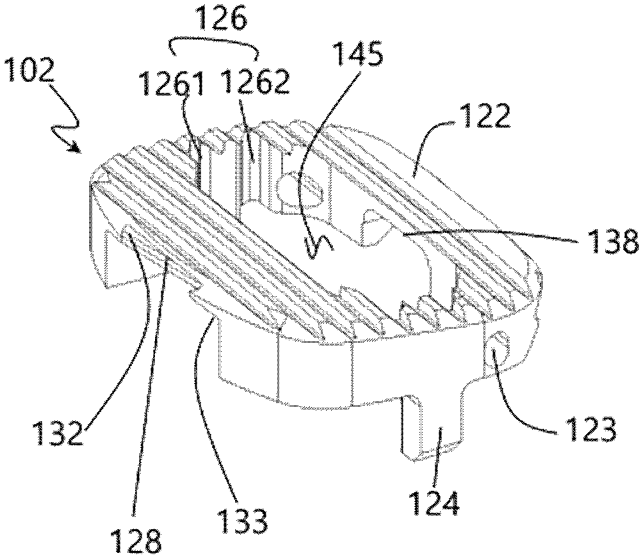
FIG. 10 is a top front perspective view of the first end plate of the first embodiment.
Figure 11:
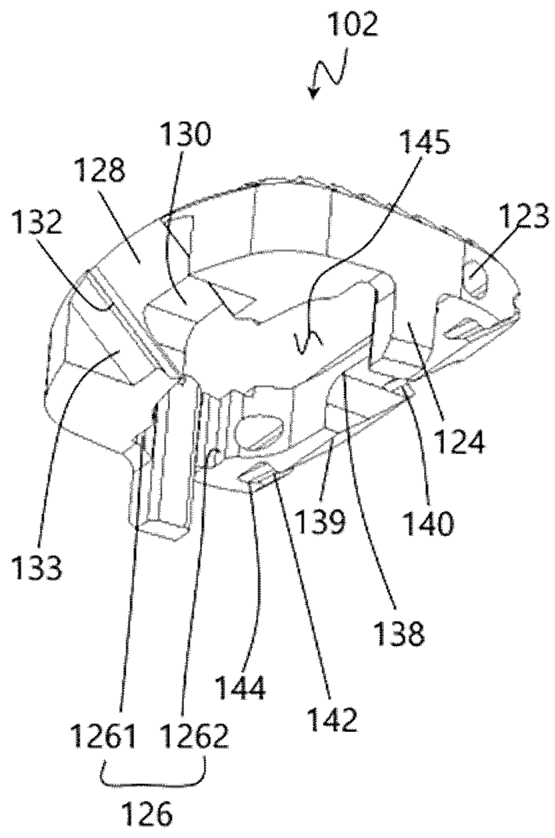
FIG. 11 is a bottom rear perspective view of the first end plate of FIG. 7.
Figure 12:
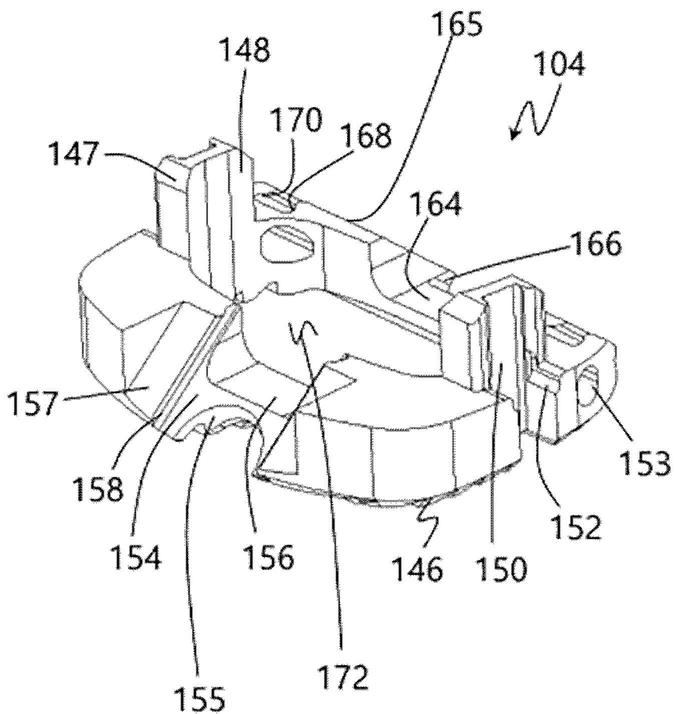
FIG. 12 is a top front perspective view of the second end plate of the first embodiment.
Figure 13:
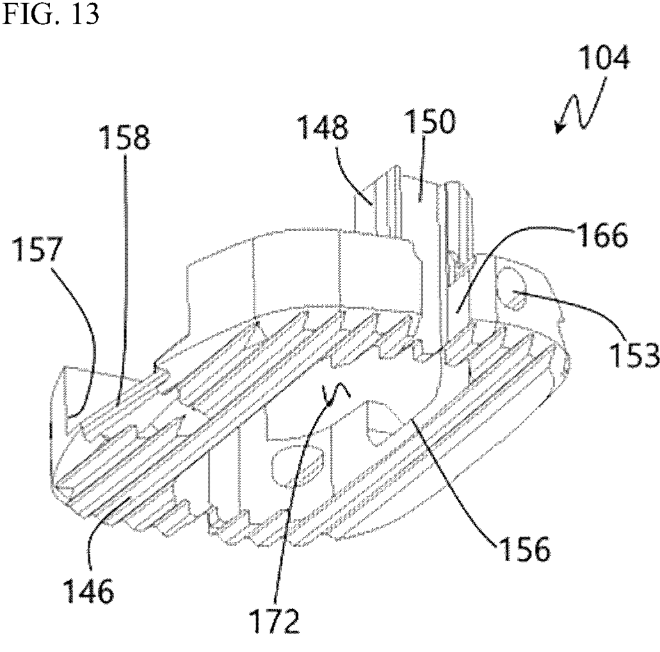
FIG. 13 is a bottom rear perspective view of the second end plate of FIG. 12.

As illustrated in FIGS. 10 and 11, the vertical guide portion includes a first vertical guide formed in the thickness direction of the first end plate 102, 302 or the second end plate 122, 322, and a second vertical guide formed in the thickness direction of the first end plate 102, 302 or the second end plate 122, 322 to be slidable with the first vertical guide.

Two pairs of the vertical guides are arranged, one pair of which is arranged on one side of the first end plate 102, 302 and the second end plate 122, 322 in the width direction, and the other pair of which is arranged on the other side of the first end plate 102, 302 and the second end plate 122, 322 in the width direction. The following three cases are possible. First, the first vertical guide is installed on both sides of the first end plate 102, 302, and the second vertical guide is installed on both sides of the second end plate 122, 322. Second, the second vertical guide is installed on both sides of the first end plate 102, 302, and the first vertical guide is installed on both sides of the second end plate 122, 322. Third, the first vertical guide and the second vertical guide are installed on both sides of the first end plate 102, 302, respectively, and the second vertical guide and the first vertical guide are installed on both sides of the second end plate 122, 322 to correspond to those of the first end plate 102, 302. Hereinafter, the first case is described as an example.

The first vertical guide is a pillar 124, 324 protruding from the first end plate 102, 302 in the thickness direction, and the second vertical guide has a channel 150, 350 surrounding part of the outer surface of the pillar 124, 324.

An accommodation portion 126, 326 is formed around the pillar 124, 324. The accommodation portion 126, 326 is a space in which the extension portion 148, 348 described below is accommodated. A first accommodation groove 1261, 3261 is formed on the proximal side, and a second accommodation groove 1262, 3262 is formed on the distal side.

The channel 150, 350 is formed by a first recessed portion concavely arranged in the second end plate 104, 304 in the width direction, and a second recessed portion formed by an extension portion 148, 348 protruding from the recessed portion in the thickness direction of the second end plate 104, 304.

Here, a guide portion 147 is formed at an upper end of the extension portion 148 of the first embodiment so that the extension portion 148 can be easily inserted into the accommodation portion 126. A cut-off portion 349 is formed in the extension portion 348 of the second embodiment in the proximal direction. The cut-off portion is formed to prevent interference with the extension portion 348 when a bone screw 320 is inserted.

Figure 14:
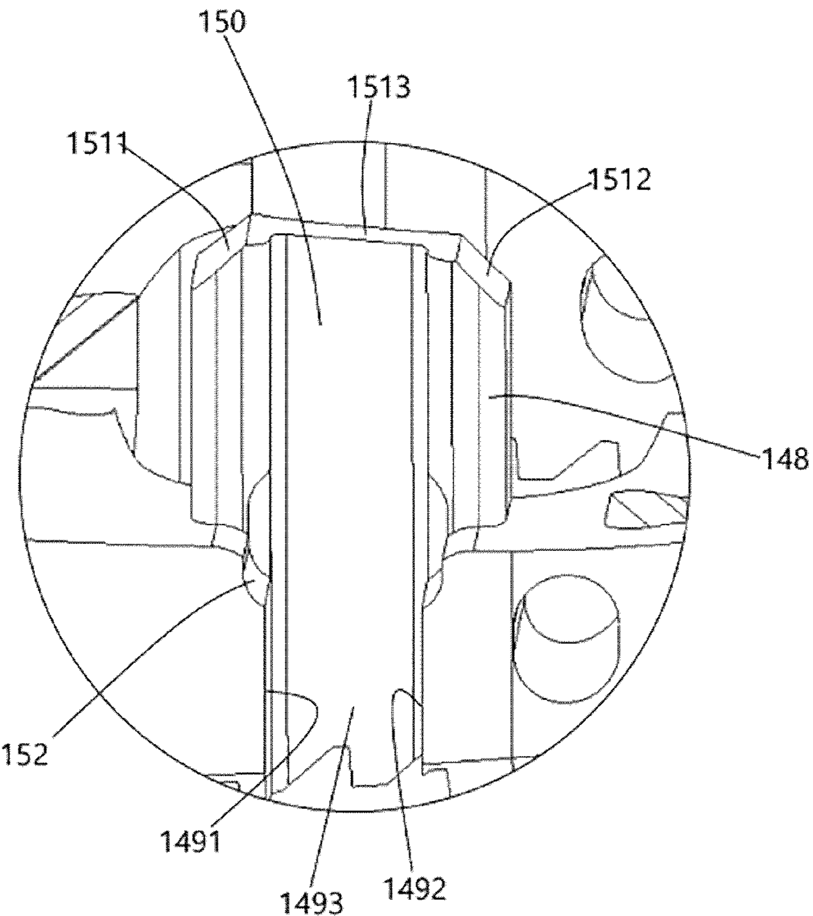
FIG. 14 is a partially enlarged view of the vertical guide of the second end plate of FIG. 12.
Figure 15:
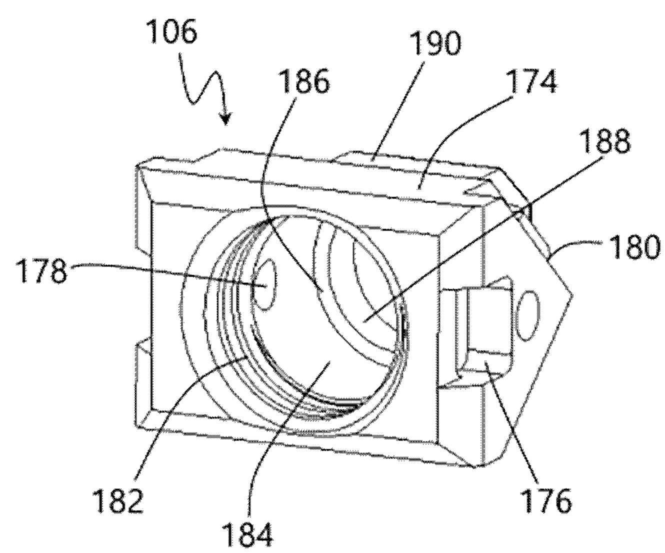
FIG. 15 is a top front perspective view of a proximal movable block of the first embodiment.
Figure 16:
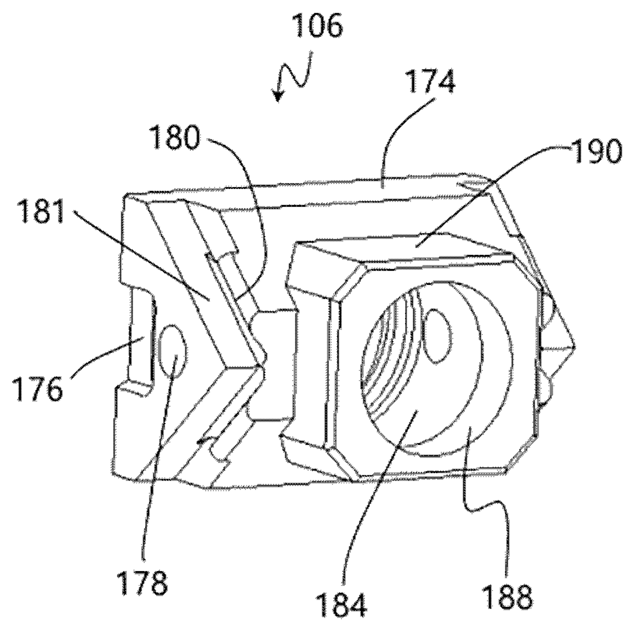
FIG. 16 is a top rear perspective view of the proximal movable block of FIG. 15.
Figure 17:
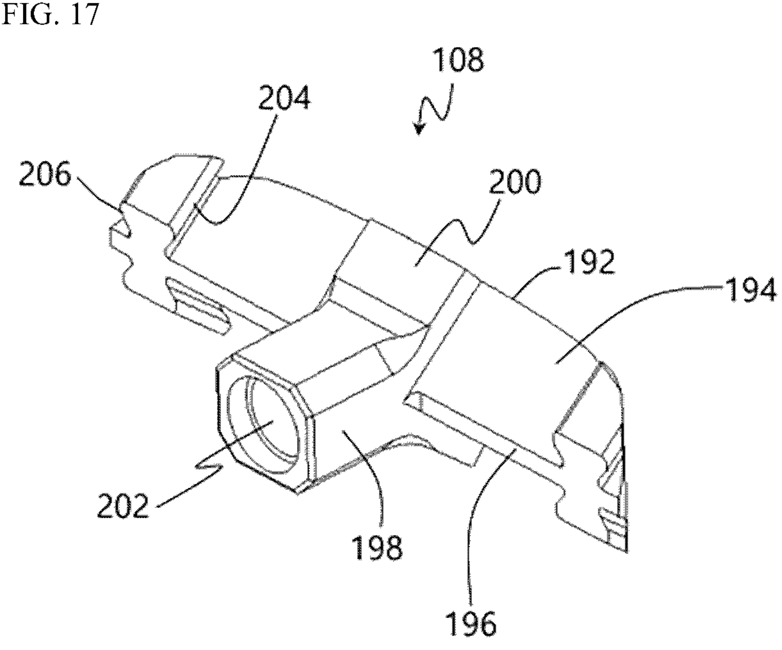
FIG. 17 is a top front perspective view of a distal movable block of the first embodiment.
Figure 18:
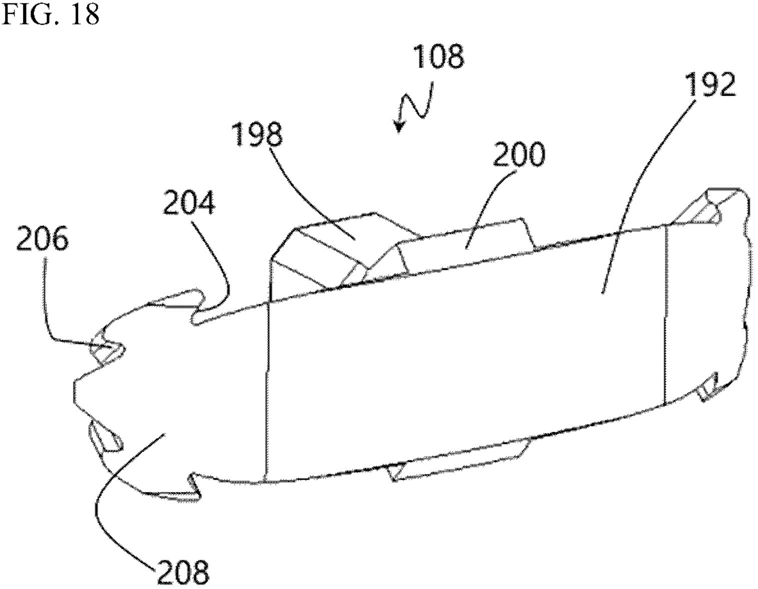
FIG. 18 is a top rear perspective view of the distal movable block of FIG. 17.

As illustrated in FIG. 14, the first recessed portion is concavely formed by a first recessed wall 1491, 3491 disposed on the side of the proximal portion, a second recessed wall 1492, 3492 spaced apart from the first recessed wall 1492, 3492 and disposed on the side of the distal portion, and a third recessed wall 1493, 3493 connecting the first recessed wall 1491, 3491 and the second recessed wall 1492, 3492.

The second recessed portion is formed by an extension portion 148, 348 including a first extension wall 1511, 3511 protruding from the second end plate 104, 304 in the thickness direction and disposed on the side of the proximal portion, a second extension wall 1512, 3512 protruding from the second end plate 104, 304 in the thickness direction and disposed on the side of the distal portion, and a third extension wall 1513, 3513 protruding from the second end plate 104, 304 in the thickness direction and connecting the first extension wall 1511, 3511 and the second extension wall 1512, 3512.

Accordingly, the first recessed portion and the second recessed portion form a substantially U shape. The first extension wall 1511, 3511 and the first recessed wall 1491, 3491 form a plane, the second extension wall 1512, 3512 and the second recessed wall 1492, 3491 form a plane, and the third extension wall 1513, 3513 and the third recessed wall 1493, 3493 form a plane. As a result, the first recessed portion and the second recessed portion form a channel 150, 350 as a whole, and the pillar 124, 324 is slidable relative to the channel 150, 350.

The depth of the second recessed portion in the width direction is smaller than the depth of the first recessed portion in the width direction. Here, the thickness of the pillar 120, 324 in the width direction is the same as the depth of the first recessed portion in the width direction, and the thickness of the pillar 124, 324 in the longitudinal direction is the same as the distance between the first recessed wall 1491, 3491 and the second recessed wall 1492, 3492 in the longitudinal direction.

Accordingly, when the pillar 124, 324 is inserted into the channel 150, 350, the first recessed portion surrounds two surfaces in the longitudinal direction and one surface in the width direction of the pillar 124, 324, whereas the second recessed portion surrounds the whole of one surface in the width direction but part of two surfaces in the longitudinal direction of the pillar 124, 324.

In addition, in order to support a force applied in the longitudinal direction, preferably, the sum of the thicknesses of the first extension wall 1511, 3511 and the second extension wall 1512, 3512 in the longitudinal direction is greater than or equal to the thickness of the pillar in the longitudinal direction. In order to maximize a force applied in the width direction, preferably, the thickness of the third extension wall 1513, 3513 in the width direction is the same as the thickness of the pillar 124, 324 in the width direction.

A guide groove 152, 352 for guiding the insertion of the pillar 124, 324 is formed around the first recessed portion, such that the pillar 124, 324 is naturally guided to the side of the first recessed portion when the spinal fusion cage 100, 300 is assembled or the height thereof is lowered after being raised.

Next, the difference in structure between the spinal fusion cage 100 in the first embodiment and the spinal fusion cage 300 in the second embodiment will be described.

With regard to the spinal fusion cage 100 in the first embodiment, a center groove 155 is formed in the proximal portion of the first end plate 102 or the second end plate 104. In the first embodiment, a center groove 155 is formed only in the second end plate 104.

Figure 6:
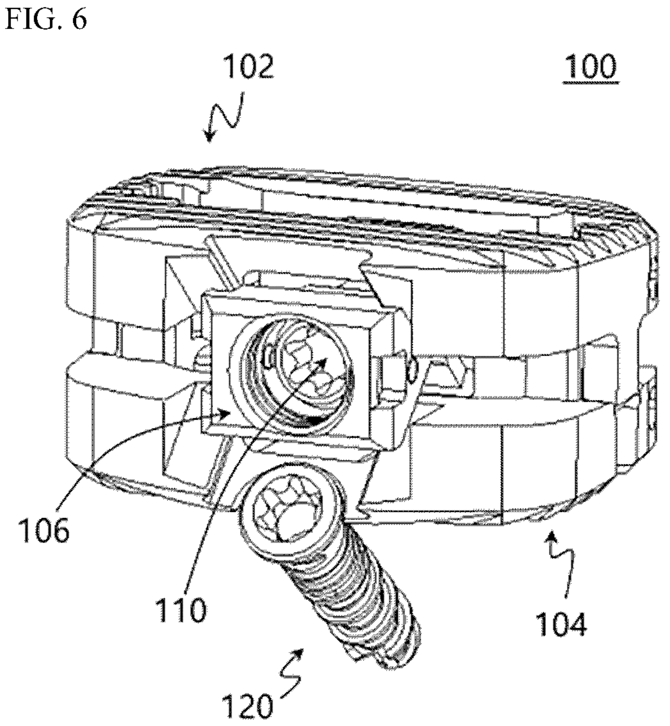
FIG. 6 is a top front perspective view of a state in which a bone screw is inserted around the center groove in the spinal fusion cage of FIG. 3.

The center groove 155 has a first plate body 122 or a second plate body 146 of the proximal portion formed in order to prevent the spinal fusion cage 100 from being separated in the opposite direction of the insertion direction after the spinal fusion cage 100 is inserted between vertebral bodies. As illustrated in FIG. 6, the center groove 155 is inserted into the vertebral body allowing a bone screw 120 to hang thereon. The bone screw 120 comprises a threaded portion 240 formed with a screw thread, a screw head 236 formed on one side of the threaded portion 240, and a tool groove 238 formed on the screw head 236 to be coupled with a tool such as a screwdriver.

Figure 5:
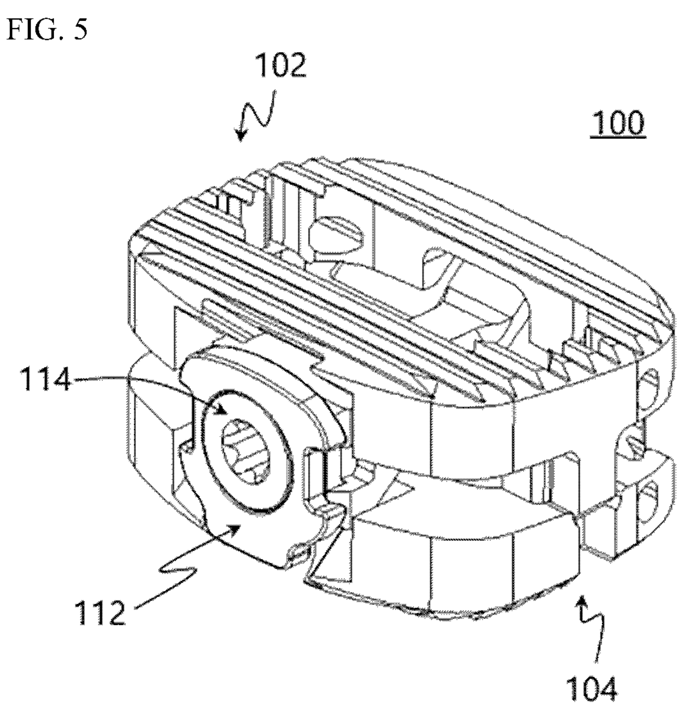
FIG. 5 is a top front perspective view of a state in which a cover plate is mounted on the spinal fusion cage in the state of FIG. 3.
Figure 7:
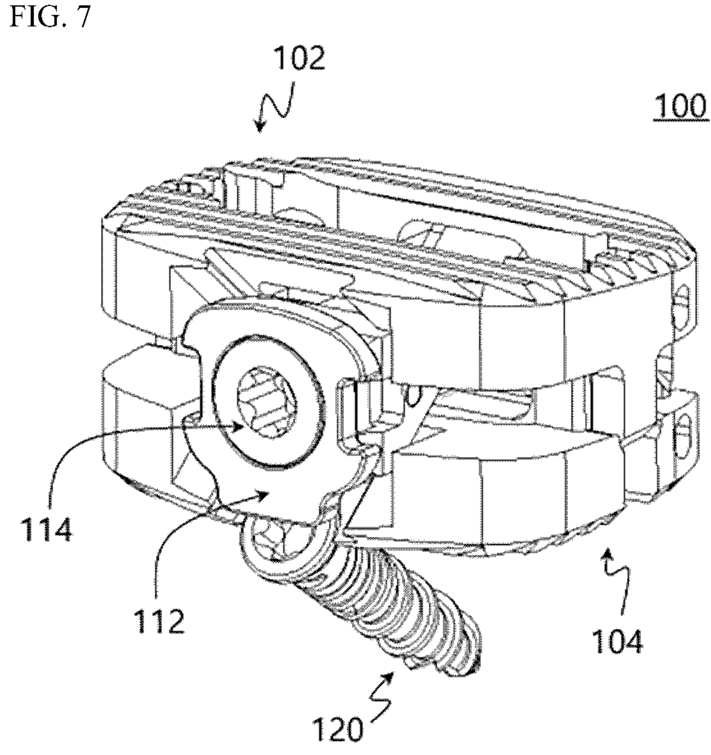
FIG. 7 is a top front perspective view of a state in which a cover plate is mounted on the spinal fusion cage in the state of FIG. 6.
Figure 8:
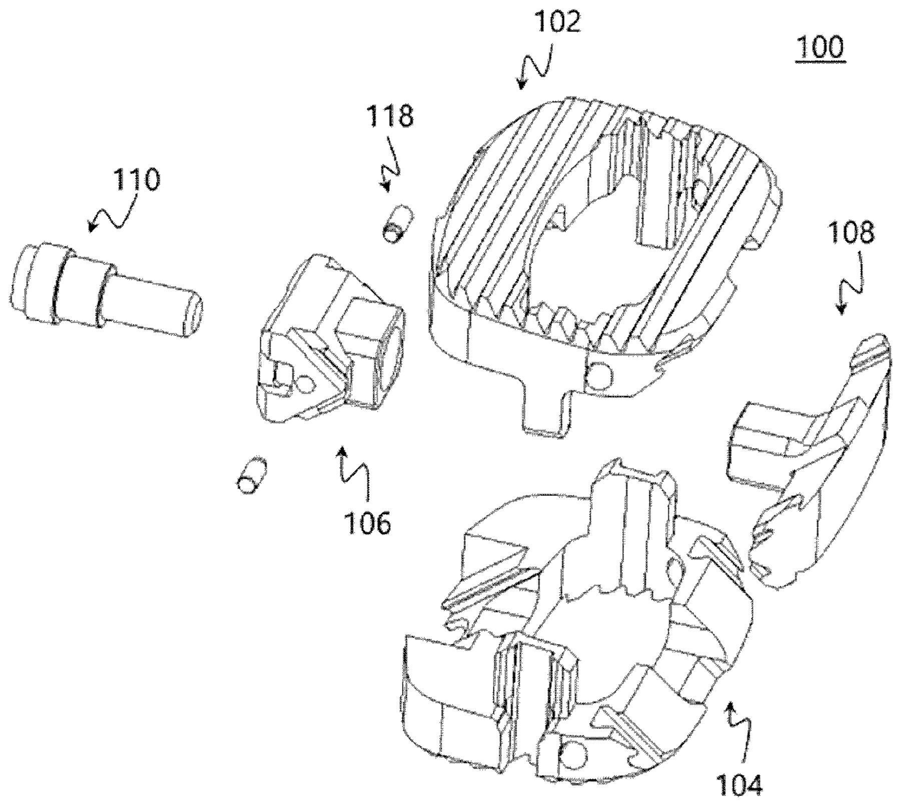
FIG. 8 is an exploded top front perspective view of the spinal fusion cage of the first embodiment.
Figure 9:
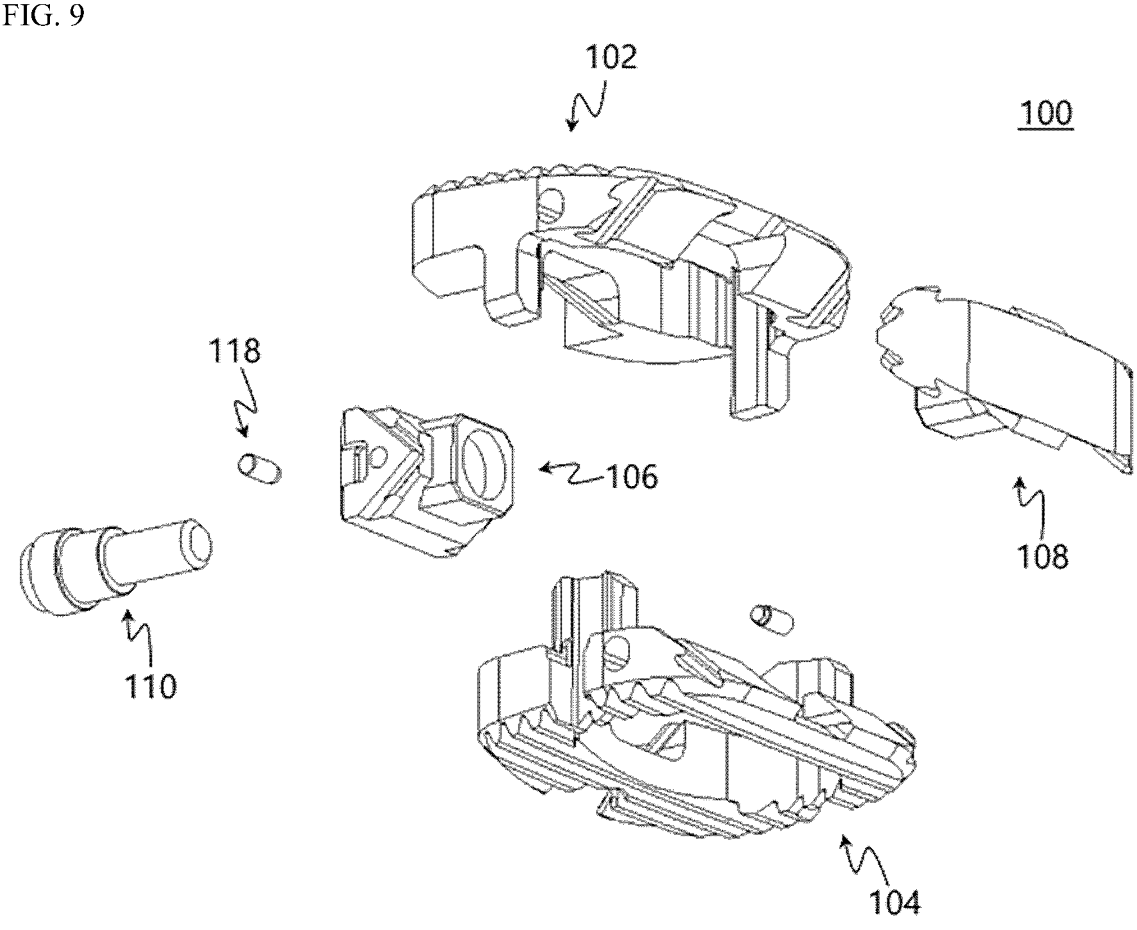
FIG. 9 is an exploded top rear perspective view of the spinal fusion cage of the first embodiment.

As illustrated in FIG. 7, a cover plate 112 is installed on the proximal movable block 106 to cover the bone screw 120. As illustrated in FIG. 5, it is possible to use the cover plate 112 in a state in which the bone screw 120 is not installed. Through this, it is possible to prevent the exposure of the proximal movable block 106 and the center groove 155. In particular, when fixing the cover plate 112, it is possible to prevent the loosening of the adjustment member 110 as a cover bolt 114 is directly fastened to a bolt fastening portion 182 formed on the proximal movable block 106. More specifically, when the cover bolt 114 contacts the adjustment member 110 while being locked, the cover bolt 114 functions as a lock nut with respect to the adjustment member 110.

Figure 20:
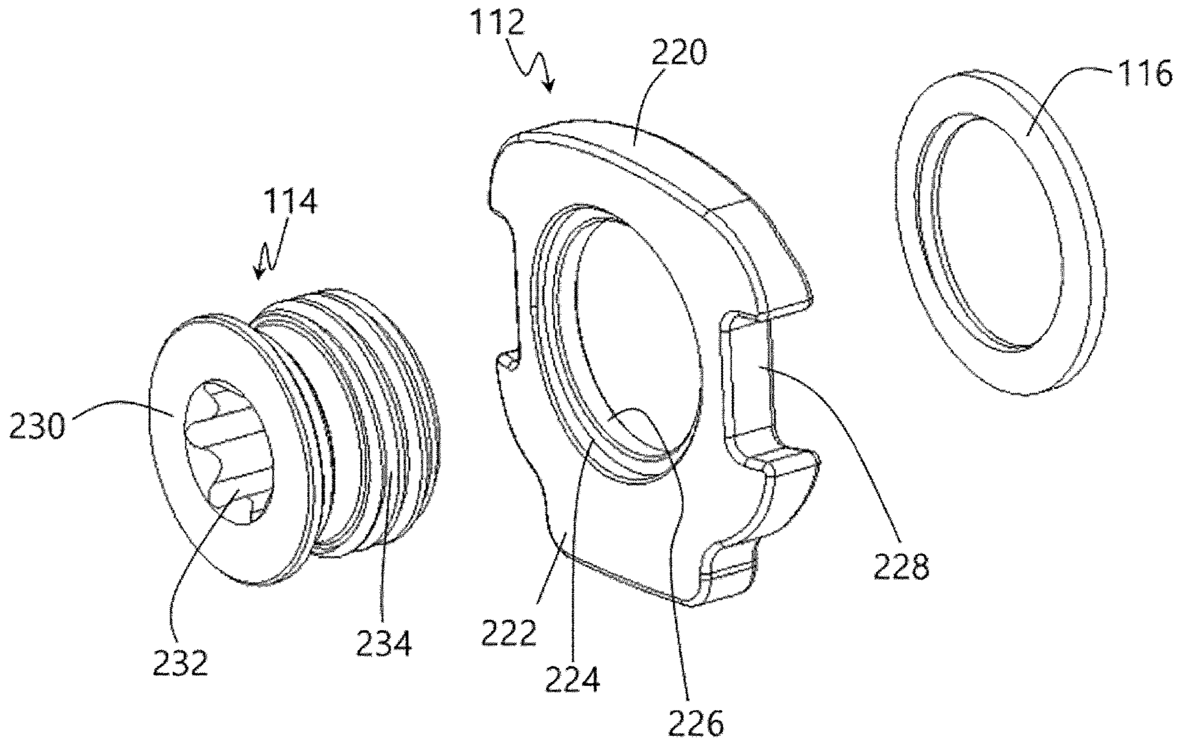
FIG. 20 is an exploded perspective view of a cover member of the first embodiment.
Figure 21:
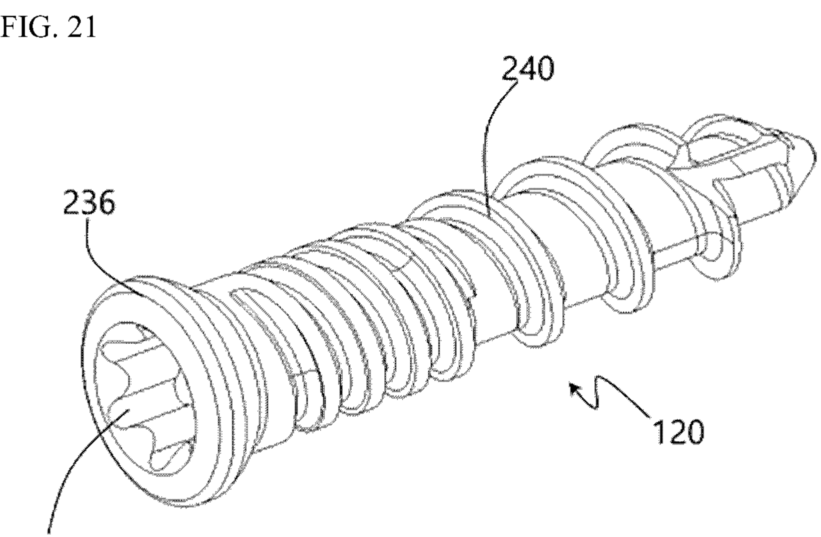
FIG. 21 is a perspective view of a bone screw of the first embodiment.
Figure 22:
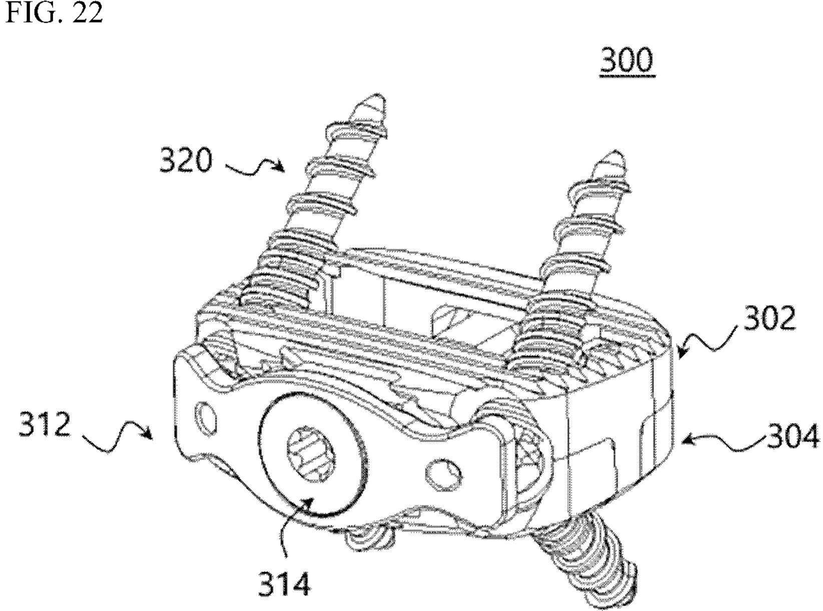
FIG. 22 is a top front perspective view of an embodiment of the spinal fusion cage according to a second embodiment in the lowest state.

The cover plate 112 and the cover bolt 114 are as illustrated in FIG. 20.

A bolt place 224 on which the cover bolt 114 is mounted and a fixing ring place 226 on which a fixing ring 116 installed to prevent the cover bolt 114 from being separated from the cover plate 112 is mounted are formed on the cover plate 112. A tool place 228 for holding the cover plate 112 by a tool is formed on a cover plate body 220 of the cover plate 112. In the first embodiment, the tool place 228 may be formed in the form of a concave groove on both sides of the cover plate body 220.

An extension portion 222 capable of covering the center groove 155 is formed on the cover plate body 220 to extend toward the first end plate 102 or the second end plate 104.

The cover bolt 114 has a cover bolt threaded portion 234 screw-coupled to the bolt fastening portion 182 of the proximal movable block 106 and a cover bolt head 230 formed at a position opposite to the cover bolt 234. A fixing ring support portion 235 is concavely formed between the cover bolt head 230 and the cover bolt threaded portion 234.

As illustrated in FIGS. 29 to 32, with respect to the spinal fusion cage 300 of the second embodiment, bone screw holes 334, 360 are respectively formed in the first end plate 302 and the second end plate 304, and a bone screw 320 penetrates the bone screw holes 334, 360 to be installed in the vertebral body.

The bone screw holes 334, 360 are formed to be sloped with respect to the longitudinal direction, and may be sloped with respect to the width direction as well. A guide surface 336, 362 guiding the bone screw 320 toward the bone screw holes 334, 360 is formed around the bone screw holes 334, 360. The bone screw 320 comprises a threaded portion 440 formed with a screw thread, a screw head 436 formed on one side of the threaded portion 440, and a tool groove 438 formed on the screw head 436 to be coupled with a tool such as a screwdriver.

In order to prevent the bone screw 320 from being separated, the spinal fusion cage 100 of the second embodiment further comprises a locking member.

Figure 27:
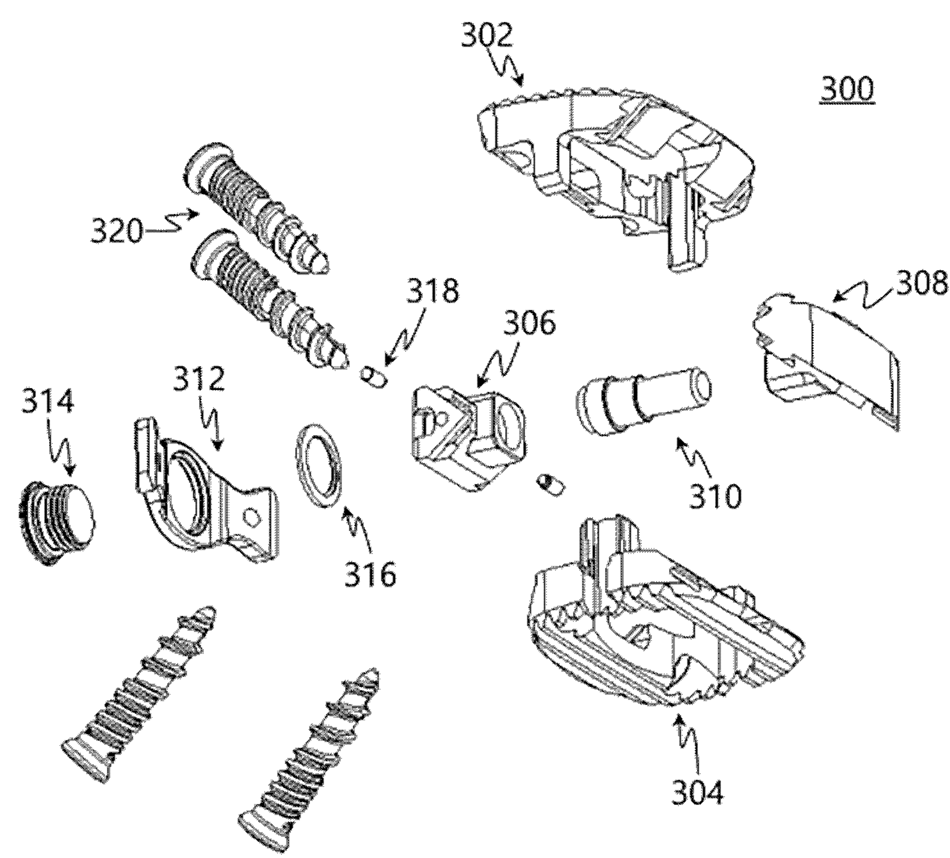
FIG. 27 is an exploded top rear perspective view of the spinal fusion cage of the second embodiment.
Figure 28:
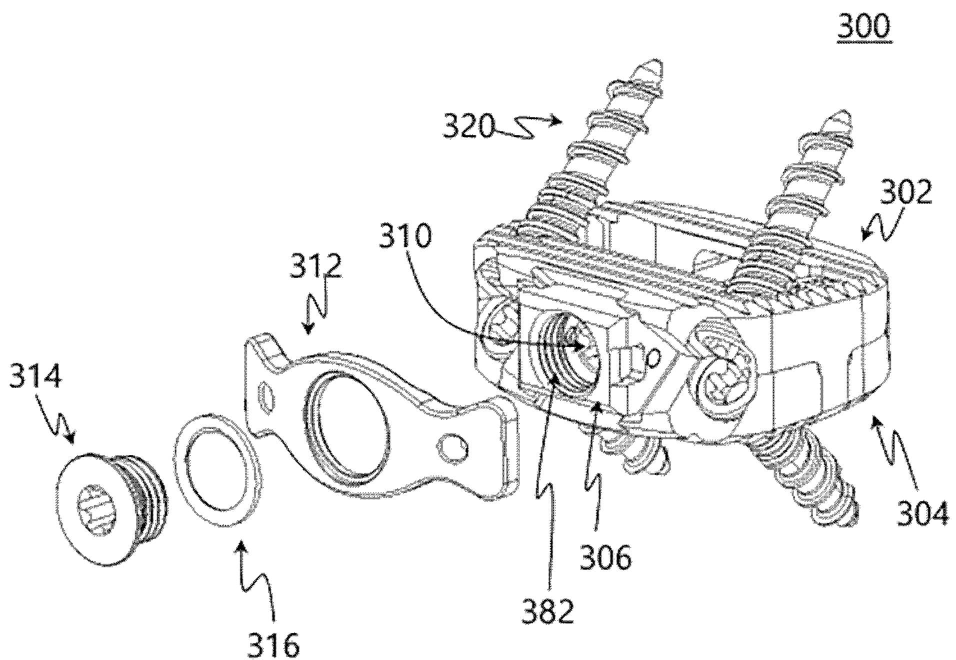
FIG. 28 is a perspective view of a state in which a locking plate of the spinal fusion cage of the second embodiment is coupled.
Figure 29:
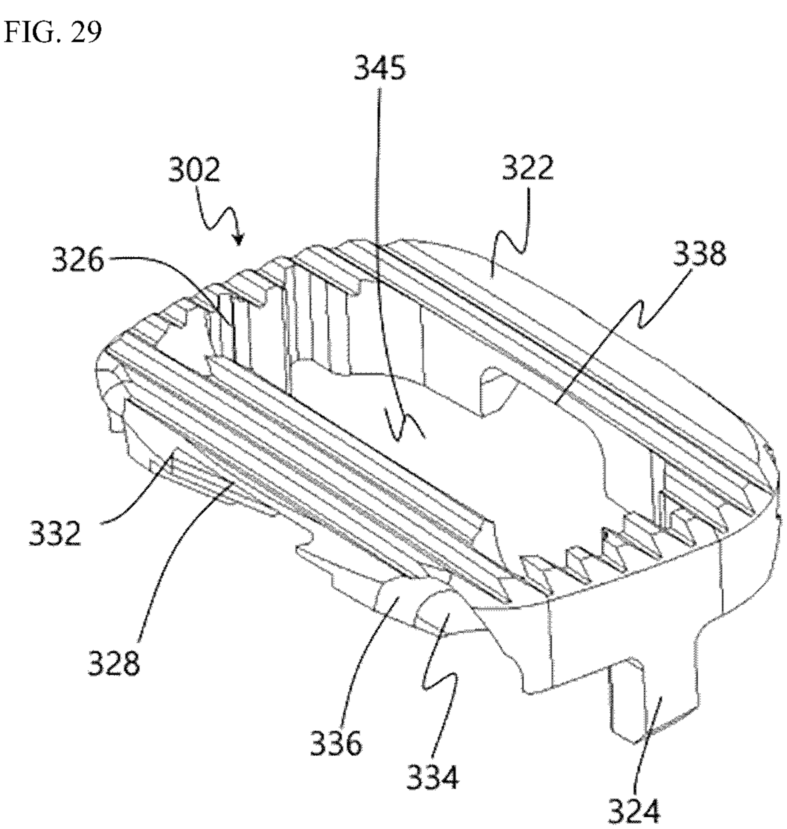
FIG. 29 is a top front perspective view of the first end plate of the second embodiment.
Figure 30:
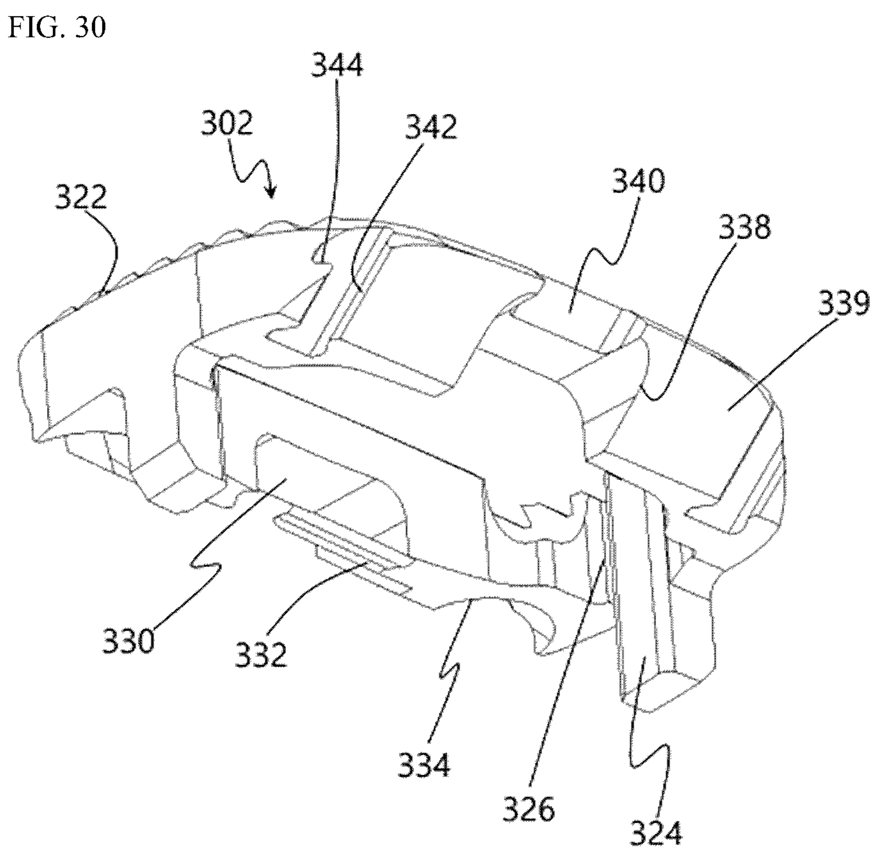
FIG. 30 is a bottom rear perspective view of the first end plate of FIG. 29.
Figure 31:
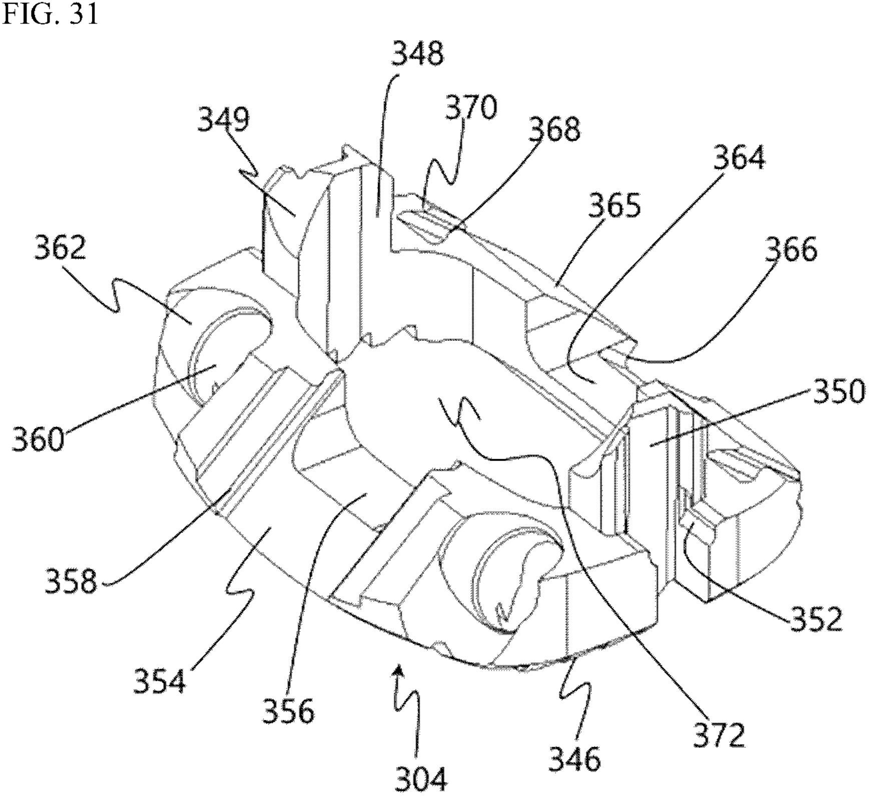
FIG. 31 is a top front perspective view of the second end plate of the second embodiment.
Figure 32:
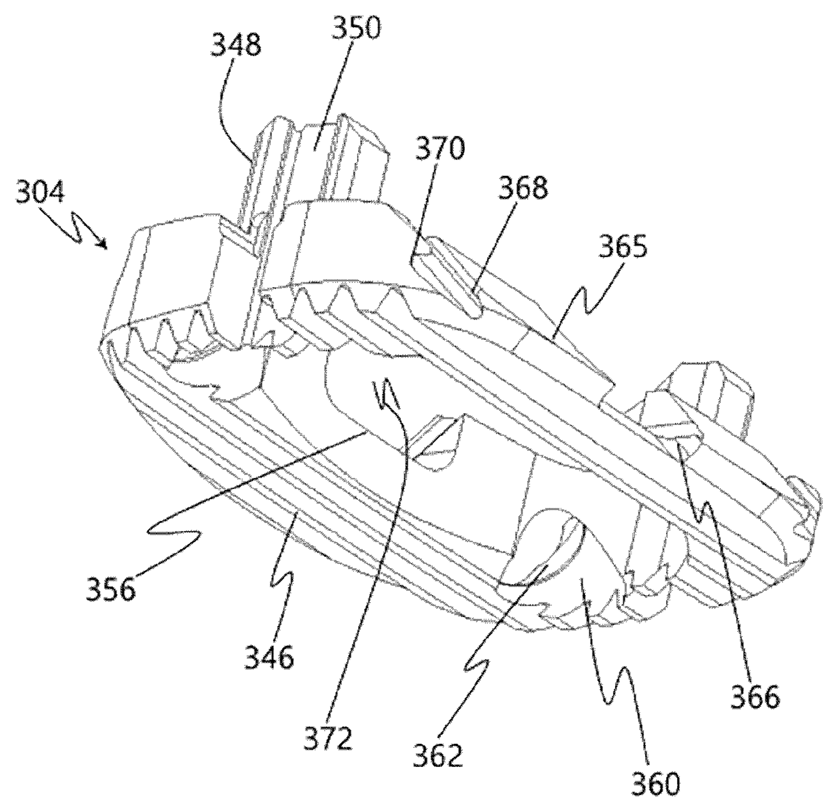
FIG. 32 is a bottom rear perspective view of the second end plate of FIG. 31.
Figure 33:
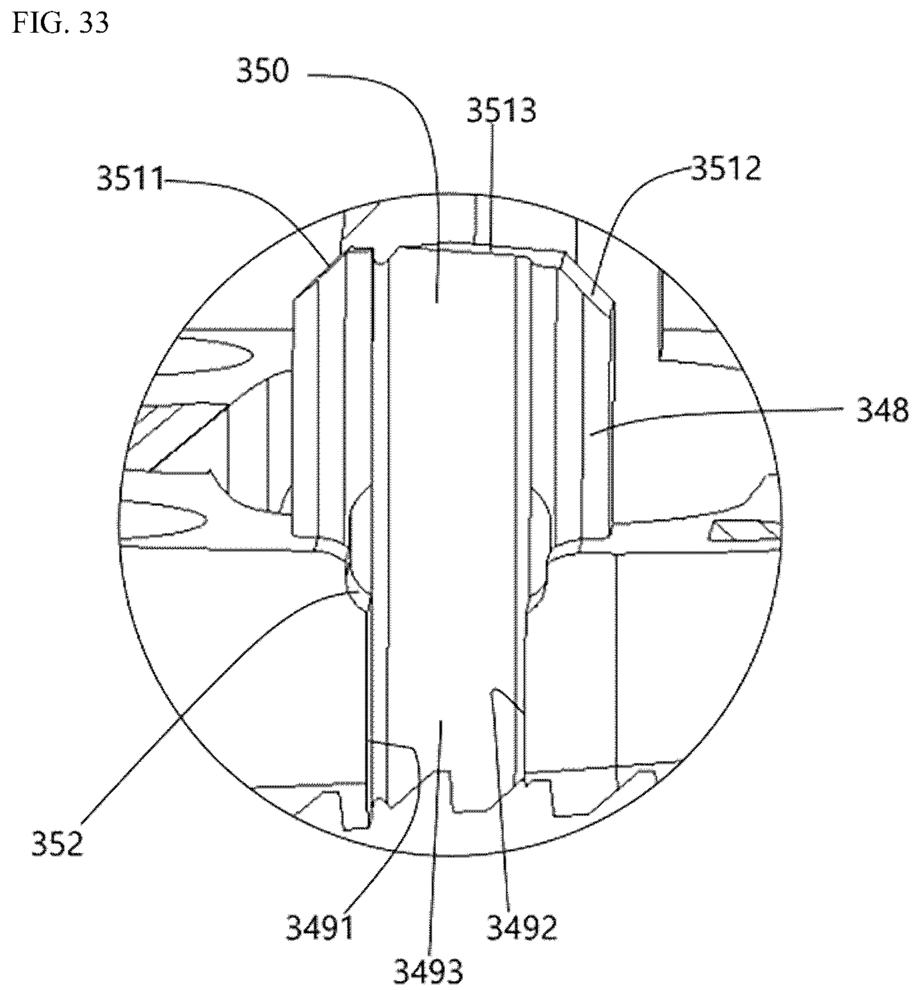
FIG. 33 is a partially enlarged view of the second end plate of FIG. 31.
Figure 34:
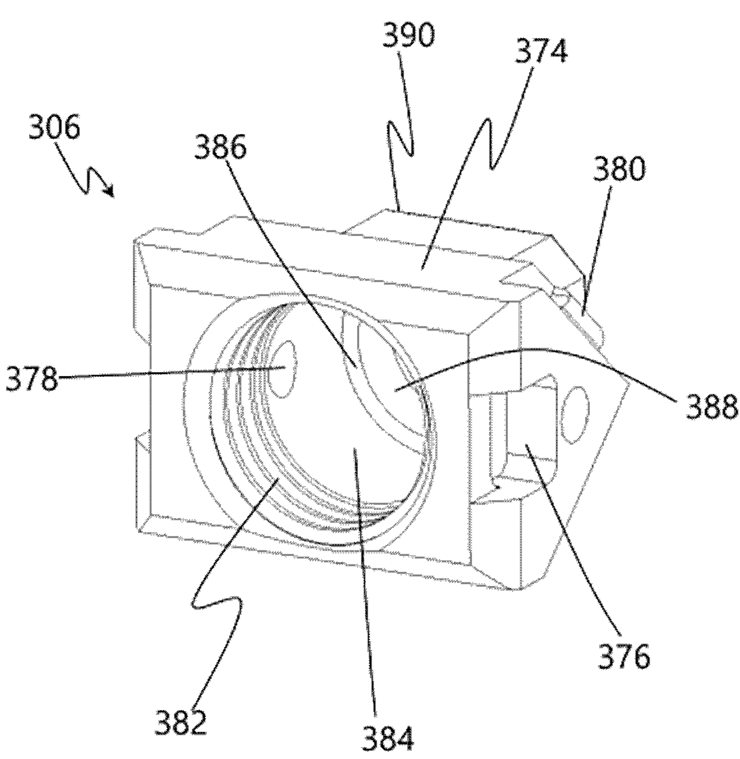
FIG. 34 is a top front perspective view of a proximal movable block of the second embodiment.
Figure 35:
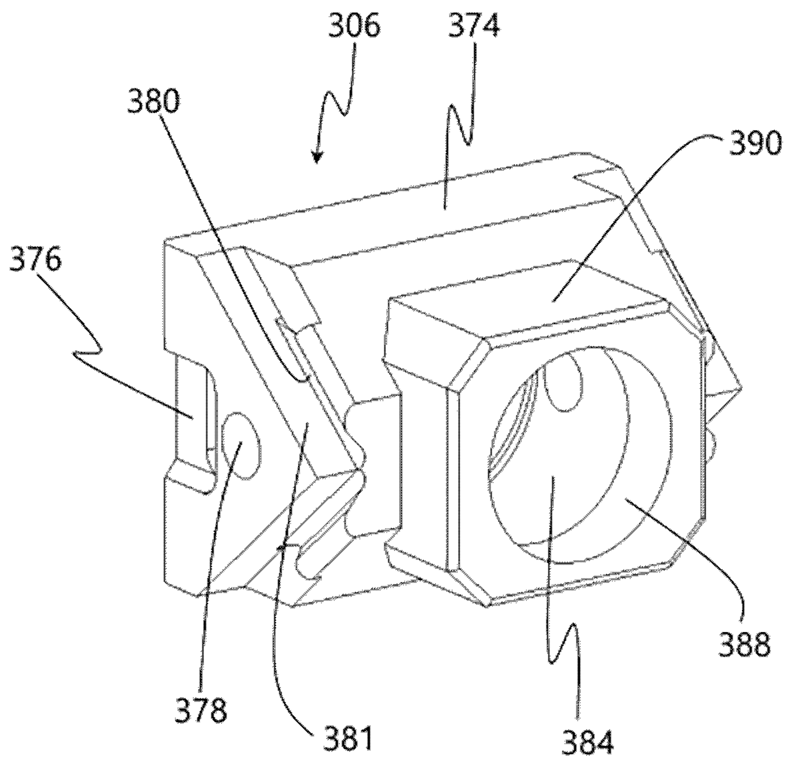
FIG. 35 is a top rear perspective view of the proximal movable block of FIG. 34.
Figure 36:
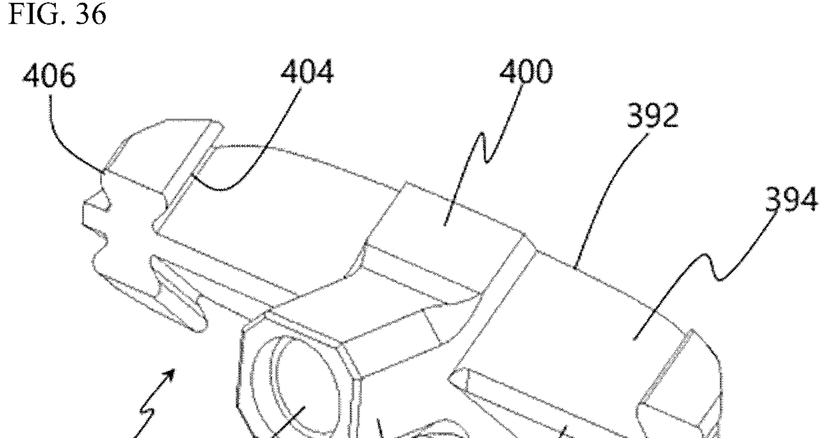
FIG. 36 is a top front perspective view of a distal movable block of the second embodiment.
Figure 37:
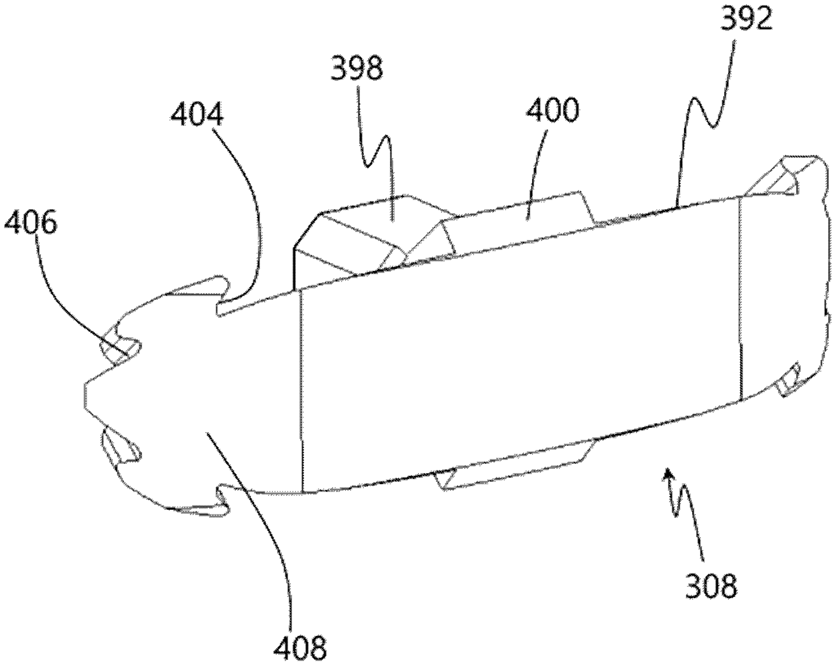
FIG. 37 is a top rear perspective view of the distal movable block of FIG. 36.

As illustrated in FIGS. 27 and 28, the locking member may comprise a locking plate 312 covering the bone screw 320, and a locking bolt 314 penetrating the locking plate 312 to be fixed to the proximal movable block 306.

Figure 39:
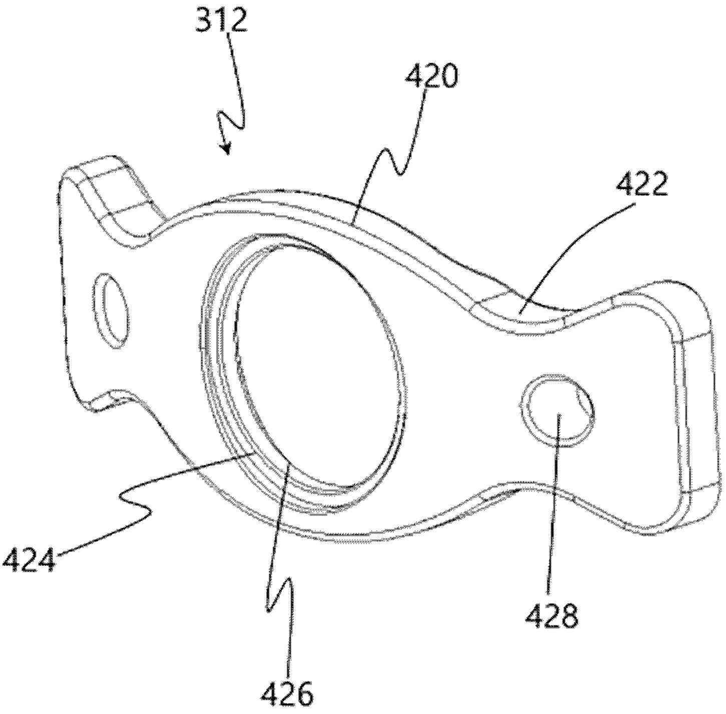
FIG. 39 is a top front perspective view of the locking plate of the second embodiment.
Figure 40:
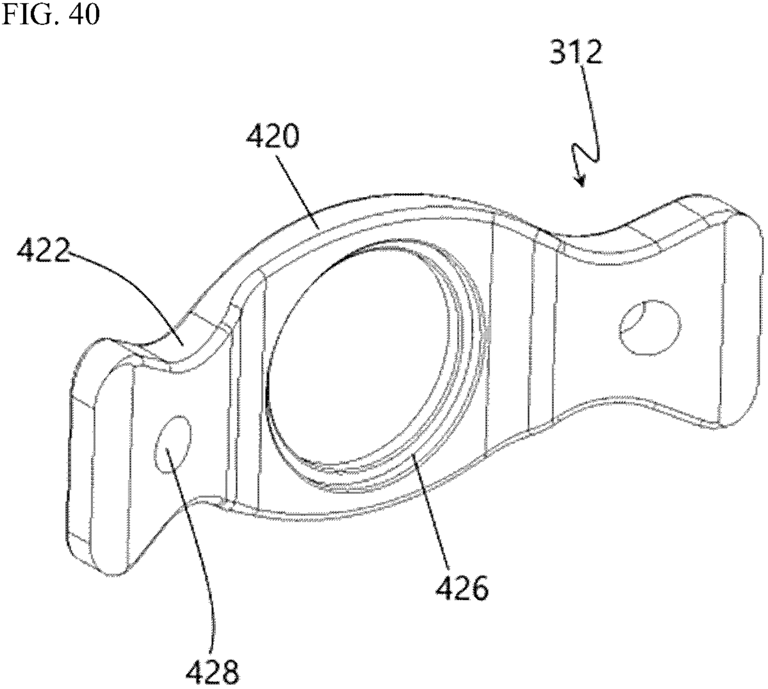
FIG. 40 is a top rear perspective view of the locking plate of FIG. 39.
Figure 41:
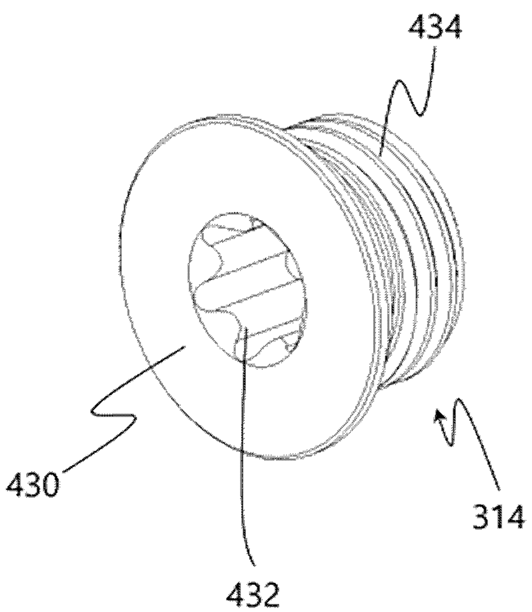
FIG. 41 is a top front perspective view of the locking bolt of the second embodiment.

As illustrated in FIGS. 39 and 40, the locking plate 312 has a substantially plate-shaped locking plate body 420, and a cover portion 422 extending on both sides of the locking plate body 420 may be formed to be slightly curved for the cover of the locking bolt 414. A tool place 428 is formed in the locking plate body 420, and the tool place 428 in the second embodiment is a hole penetrating both sides of the cover portion 422.

A locking bolt place 424 is formed in the center portion of the locking plate body 420 so that the locking bolt 114 may be mounted thereon. A fixing ring place 426 on which a fixing ring 316 may be mounted is arranged around the locking bolt place 422.

The locking bolt 114 may be screw-coupled to a bolt fastening portion 382 to which a locking bolt 314 may be coupled at a front end of the adjustment member 310 of the proximal movable block 306. When the locking bolt 314 is fastened to the proximal movable block 306, if the locking bolt 314 is in contact with the adjustment member 310, a frictional force is generated in the contact area at the time the locking bolt 314 pushes the adjustment member 310. As a result, the adjustment member 310 has the advantage that the frictional force in the screw region increases so that the adjustment member 310 is not loosened even when a load, in particular a repeated load, is applied to the first end plate 302 and the second end plate 304.

The locking bolt 314 comprises a locking bolt head 430 which may be mounted on the locking bolt place 424, a locking threaded portion 434 having a screw thread fastened to the bolt fastening portion 382, and a tool groove 432 coupled to a tool. In particular, a ring groove may be disposed in the locking bolt 314 and a fixing ring 316 may be inserted into the ring groove so that the locking bolt 314 is not separated from the locking plate 312.

The spinal fusion cage 100 and 300 is configured as described above, and a method of practicing the spinal fusion cage 100 will be described below.

First, a surgical path to the vertebral body is secured using a surgical instrument, and the target disk is removed. Then, in a state in which the spinal fusion cage 100 is held by a cage holder (not shown), the spinal fusion cage 100, 300 is inserted between the vertebral body from which the disk has been removed.

Then, the proximal movable block 106, 306 and the distal movable block 108, 308 are brought close to each other by inserting a tool such as a screwdriver into a tool groove 216, 416 of the adjustment member 110, 310, and rotating in one direction. As a result, the first end plate 102, 302 and the second end plate 104, 304 are spaced apart from each other.

In the case of the first embodiment, a bone screw 120 is installed in the center groove 155. In the case of the second embodiment, a bone screw 320 is installed penetrating the bone screw hole 334, 360.

Then, in the case of the first embodiment, a cover plate 112 is installed on the proximal movable block 106 by a cover bolt 114. In the case of the second embodiment, a locking plate 312 is installed on the proximal movable block 306 by a locking bolt 314.

When the spinal fusion cage 100, 300 is incorrectly inserted or needs to be removed for reoperation, the spinal fusion cage 100, 300 is removed in reverse order of the above-described surgical procedure.

That is, the cover plate 112 or the locking plate 312 is separated from the proximal movable block 106, 306 by loosening the cover bolt 114 or the locking bolt 314. Then, the distance between the proximal movable block 106, 306 and the distal movable block 108 is separated by rotating in the other direction by inserting a tool such as a screwdriver into the adjustment member 110, 310 in a state in which the spinal fusion cage 100, 300 is held by a cage holder (not shown). As a result, the distance between the first end plate 102, 302 and the second end plate 104, 304 is made closer so as to lower the overall height and separate it from the vertebral body.

While preferred embodiments of the present disclosure have been described as above, it will be understood by those of ordinary skill in the art that various changes in form and details may be made therein without departing from the spirit and scope of the present disclosure as defined by the following claims.

INDUSTRIAL APPLICABILITY

According to the present invention, one cage may be used for a given height range, thereby reducing the burden of inventory and production. Additionally, repetitive tasks during surgery are reduced, thereby reducing burdens on surgeons. In addition, the operation time and the amount of bleeding may be reduced, and thus the recovery time of patients may be greatly reduced. Therefore, the present disclosure may be widely used in related fields.

DESCRIPTION OF REFERENCE NUMERALS

100: spinal fusion cage
102: first end plate
104: second end plate
106: proximal movable block
108: distal movable block
110: adjustment member
112: cover plate
114: cover bolt
116: fixing ring
118: pin member
120: bone screw
122: first plate body
123: first side hole
124: pillar
126: accommodation portion
128, 139, 154, 165: plate slope portion
130, 156: proximal movable block place
132, 142, 158, 168: plate slider
133, 157: plate auxiliary support portion
138, 164: distal movable block place
140, 166: reinforcing slope portion place
144, 170: place auxiliary slider
145: first window
146: second plate body
147: guide portion
148: extension portion
150: channel
152: guide groove
153: second side hole
155: center groove
172: second window
174, 194: block slope portion
176: tool place
178: pinhole
180, 204: block slider
181: block auxiliary support portion
182: bolt fastening portion
184: support portion
186: support jaw
188: adjustment member hole
190: proximal connecting tube
192: distal wall
196: wing portion
198: distal connecting tube
200: reinforcing slope portion
202: movable block threaded portion
206: block auxiliary slider
208: distal curved surface
210: adjustment screw fixing portion
212: adjustment screw support portion

214: adjustment threaded portion
216: tool groove
218: pin place
220: cover plate body
222: extension portion
224: bolt place
226: fixing ring place
228: tool place
230: cover bolt head
232: tool groove
234: cover bolt threaded portion
235: fixing ring support portion
236: bone screw head
238: tool groove
240: bone screw threaded portion
1261: first accommodation groove
1262: second accommodation groove
1491: first recessed wall
1492: second recessed wall
1493: third recessed wall
1511: first extension wall
1512: second extension wall
1513: third extension wall
300: spinal fusion cage
302: first end plate
304: second end plate
306: proximal movable block
308: distal movable block
310: adjustment member
312: locking plate
314: locking bolt
316: fixing ring
318: pin member
320: bone screw
322: first plate body
323: first side hole
324: pillar
326: accommodation portion
328, 339, 354, 365: plate slope portion
330, 356: proximal movable block place
332, 342, 358, 368: plate slider
333, 357: plate auxiliary support portion
334, 360: bone screw hole
336, 362: guide surface
338, 364: distal movable block place
340, 366: reinforcing slope portion place
344, 370: plate auxiliary slider
345: first window
346: second plate body
348: extension portion
349: cut-off portion
350: channel
352: guide groove
353: second side hole
372: second window
374, 394: block slope portion
376: tool place
378: pin hole
380, 404: block slider
381: block auxiliary support portion
382: bolt fastening portion
384: support portion
386: support jaw
388: adjustment member hole
390: proximal connecting tube
392: distal wall
398: distal connecting tube
400: reinforcing slope portion
402: movable block threaded portion
406: block auxiliary slider
408: distal curved surface
410: adjustment screw fixing portion
412: adjustment screw support portion
414: adjustment threaded portion
416: tool groove
418: pin place
420: cover plate body
422: wing portion
424: bolt place
426: fixing ring place
428: tool place
430: cover bolt head
432: tool groove
434: cover bolt threaded portion
435: fixing ring support portion
3261: first accommodation groove
3262: second accommodation groove
3491: first recessed wall
3492: second recessed wall
3493: third recessed wall
3511: first extension wall
3512: second extension wall
3513: third extension wall

What is claimed is:

1. A spinal fusion cage for anterior lumbar interbody fusion, comprising:

a first end plate and a second end plate which are configured to be in contact with adjacent vertebral bodies, wherein the first end plate has a first window formed at a central portion, and the second end plate has a second window formed at a central portion;

a distal movable block connected to be movable relative to distal portions of the first end plate and the second end plate;

a proximal movable block connected to be movable relative to proximal portions of the first end plate and the second end plate;

an adjustment member capable of adjusting the distance between the distal movable block and the proximal movable block by adjusting the distance between the proximal movable block and the distal movable block by rotation; and a vertical guide portion disposed in the first end plate and the second end plate, to support a load in the longitudinal direction or width direction of the first end plate and the second end plate, wherein a block slider is formed on each of the distal movable block and the proximal movable block, and a plate slider slidable relative to the block slider is formed on each of the first and second end plates, and the maximum distance of the block slider of the distal movable block from the axis of the adjustment member in the width direction is longer than the maximum distance of the block slider of the proximal movable block from the axis of the adjustment member in the width direction, and wherein the maximum distance of the block slider of the proximal movable block in the width direction is shorter than the maximum distance of the first window and the second window in the width direction, wherein both widthwise ends of the block slider of the proximal movable block are located within the width of the first window and the second window, wherein the maximum width of the distal movable block is longer than the maximum width of the proximal movable block.

2. The spinal fusion cage for anterior lumbar interbody fusion of claim 1, wherein a block auxiliary slider is disposed around the distal movable block, and a plate auxiliary slider sliding on the block auxiliary slider is formed on the first and second end plates.

3. The spinal fusion cage for anterior lumbar interbody fusion of claim 2, wherein the block auxiliary slider is disposed at the end of the distal movable block in the width direction.

4. The spinal fusion cage for anterior lumbar interbody fusion of claim 2, wherein the block auxiliary slider is disposed in a direction opposite to the block slider.

5. The spinal fusion cage for anterior lumbar interbody fusion of claim 1, wherein the adjustment member has a threaded portion screw-coupled to the distal movable block on an end thereof, and a pin place fixed to be rotatable relative to the proximal movable block on the other end thereof, wherein a pin member is positioned in the pin place through the proximal movable block.

6. The spinal fusion cage for anterior lumbar interbody fusion of claim 1, wherein the vertical guide portion has a first vertical guide formed in a thickness direction of the first end plate or the second end plate, and a second vertical guide formed in a thickness direction of the other of the first end plate or the second end plate to be slidable with the first vertical guide, wherein two pairs of the vertical guides are arranged, one pair of the vertical guides is arranged on one side of the first end plate and the second end plate in the width direction, and the other pair of the vertical guides is arranged on the other side of the first end plate and the second end plate in the width direction.

7. The spinal fusion cage for anterior lumbar interbody fusion of claim 6, wherein the first vertical guide is a pillar protruding from the first or second end plate in the thickness direction, and the second vertical guide has a channel surrounding part of the outer surface of the pillar.

8. The spinal fusion cage for anterior lumbar interbody fusion of claim 7, wherein the channel is formed by a first recessed portion arranged concavely in the first or second end plate in the width direction, and a second recessed portion formed by an extension portion protruding from the recessed portion in the thickness direction of the first or second end plate.

9. The spinal fusion cage for anterior lumbar interbody fusion of claim 8, wherein an accommodation portion accommodating the extension portion is formed around the pillar.

10. The spinal fusion cage for anterior lumbar interbody fusion of claim 8, wherein the first recessed portion is formed concavely by a first recessed wall disposed on the side of the proximal portion, a second recessed wall spaced apart from the first recessed wall and disposed on the side of the distal portion, and a third recessed wall connecting the first recessed wall and the second recessed wall.

11. The spinal fusion cage for anterior lumbar interbody fusion of claim 10, wherein the thickness of the pillar in the width direction is the same as the depth of the first recessed portion in the width direction, and the thickness of the pillar in the longitudinal direction is the same as the distance between the first recessed wall and the second recessed wall in the longitudinal direction.

12. The spinal fusion cage for anterior lumbar interbody fusion of claim 8, wherein the second recessed portion is formed by an extension portion comprising a first extension wall protruding from the first or second end plate in the thickness direction and disposed on the side of the proximal portion, a second extension wall protruding from the first or second end plate in the thickness direction and disposed on the side of the distal portion, and a third extension wall protruding from the first or second end plate in the thickness direction and connecting the first extension wall and the second extension wall, wherein the first extension wall and the first recessed wall form a plane, the second extension wall and the second recessed wall for a plane, and the third extension wall and the third recessed wall form a plane.

13. The spinal fusion cage for anterior lumbar interbody fusion of claim 12, wherein the depth of the second recessed portion in the width direction is smaller than the depth of the first recessed portion in the width direction.

14. The spinal fusion cage for anterior lumbar interbody fusion of claim 12, wherein the sum of the thickness of the first extension wall and the second extension wall in the longitudinal direction is greater than or equal to the thickness of the pillar in the longitudinal direction.

15. The spinal fusion cage for anterior lumbar interbody fusion of claim 12, wherein the thickness of the third extension wall in the width direction is the same as the thickness of the pillar in the width direction.

16. The spinal fusion cage for anterior lumbar interbody fusion of claim 8, wherein a guide groove guiding the insertion of the pillar is formed around the first recessed portion.

17. The spinal fusion cage for anterior lumbar interbody fusion of claim 1, wherein a through-hole is disposed on the side portion of the first and second end plates.

18. The spinal fusion cage for anterior lumbar interbody fusion of claim 1, wherein a center groove is disposed at an end of the proximal side of the first or second end plate.

19. The spinal fusion cage for anterior lumbar interbody fusion of claim 18, wherein a cover member is installed on the proximal movable block.

20. The spinal fusion cage for anterior lumbar interbody fusion of claim 19, wherein the cover member comprises a cover plate covering the center groove, and a cover bolt penetrating the cover plate to be fixed to the proximal movable block.

21. The spinal fusion cage for anterior lumbar interbody fusion of claim 20, wherein an extension portion covering the center groove is formed on the cover plate.

22. The spinal fusion cage for anterior lumbar interbody fusion of claim 1, comprising:

at least two bone screws, one of which is inserted through a bone screw hole in the first end plate and another of which is inserted through a bone screw hole in the second end plate;

a locking member fastened to the proximal movable block to prevent the bone screws from being separated.

23. The spinal fusion cage for anterior lumbar interbody fusion of claim 22, wherein the locking member comprises a locking plate covering the bone screws, and a locking bolt penetrating the locking plate to be fixed to the proximal movable block, wherein a locking bolt fastening portion capable of coupling the locking bolt to a front end of the adjustment member is formed on the proximal movable block.

24. The spinal fusion cage for anterior lumbar interbody fusion of claim 23, wherein a locking projection protruding toward each of the bone screws is formed at a rear end of the locking plate.

25. The spinal fusion cage for anterior lumbar interbody fusion of claim 23, wherein the locking bolt adds pressure by contacting the adjustment member when coupled.

* * * * *